(12) United States Patent
Bastian et al.

(10) Patent No.: US 6,541,499 B1
(45) Date of Patent: Apr. 1, 2003

(54) ANTITHROMBOTIC AGENTS

(75) Inventors: Jolie A Bastian, Beech Grove, IN (US); Nickolay Y Chirgadze, Carmel, IN (US); Michael L Denney, Franklin, IN (US); Matthew J Fisher, Mooresville, IN (US); Robert J Foglesong, Durham, NC (US); Richard W Harper, Indianapolis, IN (US); Mary G Johnson, Durham, NC (US); Valentine J Klimkowski, Carmel, IN (US); Ho-Shen Lin, Indianapolis, IN (US); Michael P Lynch, Raleigh, NC (US); Jefferson R McCowan, Indianapolis, IN (US); Shawn C Miller, Noblesville, IN (US); Jeffrey T Mullaney, Indianapolis, IN (US); Michael E Richett, Indianapolis, IN (US); Daniel J Sall, Greenwood, IN (US); Gerald F Smith, Indianapolis, IN (US); Kumiko Takeuchi, Indianapolis, IN (US); Jennifer M Tinsley, Martinsville, IN (US); Michael R Wiley, Indianapolis, IN (US); Minsheng Zhang, Warren, NJ (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/423,147

(22) PCT Filed: Apr. 30, 1998

(86) PCT No.: PCT/US98/08755

§ 371 (c)(1),
(2), (4) Date: Jan. 21, 2000

(87) PCT Pub. No.: WO98/48800

PCT Pub. Date: Nov. 5, 1998

Related U.S. Application Data

(60) Provisional application No. 60/045,335, filed on May 1, 1997.

(51) Int. Cl.[7] .................. A61K 31/4196; C07D 249/08; C07D 417/12

(52) U.S. Cl. .................. 514/383; 514/228.2; 514/235.8; 514/322; 514/394; 514/406; 544/62; 544/139; 546/199; 548/262.8; 548/266.4; 548/306.1; 548/310.7; 548/364.7

(58) Field of Search .................. 514/383, 394, 514/228.2, 235.8, 322, 406; 548/266.4, 310.7, 262.8, 306.1, 364.7; 544/62, 139; 546/199

(56) References Cited

U.S. PATENT DOCUMENTS

| 5,294,631 A | * | 3/1994 | Franz et al. ............... 514/381 |
| 5,374,638 A | * | 12/1994 | Dhanoa et al. ............. 514/326 |
| 5,541,229 A | | 7/1996 | Narr et al. |
| 5,552,426 A | | 9/1996 | Lunn et al. |
| 5,576,343 A | | 11/1996 | Nagahara et al. |

FOREIGN PATENT DOCUMENTS

| EP | 0 802 183 | 10/1997 |
| WO | WO 96/03375 | 2/1996 |
| WO | WO 97/25033 | 7/1997 |

OTHER PUBLICATIONS

Encyclopedia of Toxicology, Waxler vol. 1 (1998) pp. 508–510.*
Introduction to Organic and Biological Chemistry, Wilbraham, (1984) p. 222.*
Robert M. Scarborough, "Chapter 8. Anticoagulant Strategies Targeting Thrombin and Factor Xa," *Annual Reports in Medicinal Chemistry*, (1995) 30, pp. 71–80.

* cited by examiner

Primary Examiner—Joseph K. McKane
Assistant Examiner—Sonya N. Wright
(74) Attorney, Agent, or Firm—Thomas E. Jackson; Arvie J. Anderson

(57) ABSTRACT

The invention relates to novel compounds of formula (I), and their pharmaceutically acceptable salts, as defined herein, processes and intermediates for their preparation, pharmaceutical formulations comprising the novel compounds of formula (I), and the use of the compounds of formula (I) as thrombin inhibitors.

10 Claims, No Drawings

ANTITHROMBOTIC AGENTS

This application claims the benefit of U.S. Provisional Application No. 60/045,335, filed May 1, 1997.

This invention relates to thrombin inhibitors which are useful anticoagulants in mammals. In particular it relates to heterocyclic derivatives having high anticoagulant activity, and antithrombotic activity. Thus, this invention relates to new inhibitors of thrombin, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin. See, for example Robert M. Scarborough, *Annual Reports in Medicinal Chemistry*, (1995), 30, 71–80.

Although the heparins and coumarins are effective anticoagulants, no commercial drug has yet emerged from the small synthetic molecules; and despite the continuing promise for this class of compounds, there still exists a need for anticoagulants which act selectively on thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high bioavailability and favorable pharmacokinetics following oral administration.

According to the invention there is provided a method of inhibiting thrombin comprising using an effective amount of a thrombin inhibiting compound of formula I (or a pharmaceutically acceptable salt thereof)

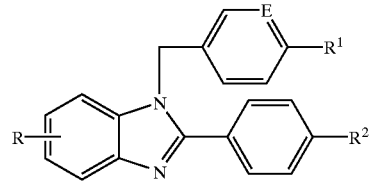

wherein
E is CH or $CR^e$ in which $R^e$ is methyl, methoxy or halo;
R denotes 0, 1 or 2 substituents on the benz-ring independently selected from halo, methyl, ethyl, hydroxy, methoxy, carbamoyl, aminomethyl and hydroxymethyl;
$R^1$ is $R^{1a}$, $R^{1b}$, or $R^{1c}$ in which
$R^{1a}$ is —$CH_2$—$R^r$, in which $R^r$ is 5-tetrazolyl, 2-carboxypyrrolidin-1-yl or 2-[[(1–4C)alkoxy]carbonyl]-pyrrolidin-1-yl; 2-carboxy-5-oxopyrrolidin-1-yl or 2-[[(1–4C)alkoxy]carbonyl]-5-oxopyrrolidin-1-yl;
$R^{1b}$ is —$X^1$—$(CH_2)_s$—$NR^sR^t$ in which $X^1$ is a direct bond, methylene or O; s is 1 or 2; provided that when s is 1, then $X^1$ is a direct bond, and further provided that the chain —$(CH_2)_s$— may bear one or two methyl or ethyl substituents or may be part of a trans-1,2-cyclohexanediyl; and $R^s$ and $R^t$ are independently hydrogen or (1–3C)alkyl or the group $NR^sR^t$ is pyrrolidino, piperidino, morpholino, 1-imidazolyl, 1-pyrazolyl, 1,2,4-triazol-1-yl, or benzylamino; and
$R^{1c}$ is —$X^1$—$(CH_2)_s$—$NR^sR^t$ in which $X^1$ is a direct bond, methylene or O; s is 1 or 2; provided that when s is 1, then $X^1$ is a direct bond, and further provided that the chain —$(CH_2)_s$— may bear one or two methyl or ethyl substituents or may be part of a trans-1,2-cyclohexanediyl; and the group $NR^sR^t$ is 2-oxopyrrolidin-1-yl, 2,5-dioxopyrrolidin-1-yl, 2-oxooxazolidin-3-yl, 2-oxoimidazolidin-1-yl, 3-methyl-2-oxoimidazolidin-1-yl, 2-oxopyrrolidin-3-yl, 1-methyl-2-oxopyrrolidin-3-yl, 1-tetrazolyl, methylsulfonylamino or phenylsulfonylamino; and
$R^2$ is $R^{2a}$, $R^{2b}$, or $R^{2c}$ in which
$R^{2a}$ is —$X^2$—$(CH_2)_n$—$R^f$ in which $X^2$ is a direct bond, methylene or O; n is 1, 2 or 3; and $R^f$ is 5-tetrazolyl, carboxy, [(1–4C)alkoxy]carbonyl or hydroxymethyl; or (provided that when n is 1, $X^2$ is a direct bond) $R^f$ is 2-carboxypyrrolidin-1-yl, 2-[[(1–4C)alkoxy]carbonyl]pyrrolidin-1-yl, (carboxymethyl)amino, [[(1–4C)alkoxy]carbonylmethyl]amino, (4-carboxymethylimidazol-1-yl)amino, [4-[[(1–4C)alkoxy]carbonylmethyl]imidazol-1-yl]amino, (4-carboxybenzyl)amino, [4-[[(1–4C)alkoxy]carbonyl]benzyl]amino, (3-amino-1,4-dioxo-4-hydroxybutyl)amino or [3-amino-1,4-dioxo-[(1–4C)alkoxy]butyl]amino;
$R^{2b}$ is —$X^2$—$(CH_2)_m$—$NR^aR^b$ in which $X^2$ is a direct bond, methylene, O or S; m is 1, 2, 3, 4 or 5; provided that when m is 1, then $X^2$ is a direct bond; and $R^a$ and $R^b$ are independently hydrogen, or (1–3C)alkyl, or one of $R^a$ and $R^b$ is hydrogen or methyl and the other is t-butyl, benzyl, or pyridylmethyl; or the group $NR^aR^b$ is pyrrolidino, piperidino, morpholino, 1-imidazolyl, 1-pyrazolyl, or 1,2,4-triazol-4-yl; or $R^{2b}$ is —[$X^2$—($CH_2$)$_n$]$_p$—N($R^a$)—CO—A in which $X^2$ is a direct bond, methylene or O; n is 1, 2, 3 or 4; p is 0 or 1, $R^a$ is hydrogen or methyl; and —CO—A is a natural or unnatural α-amino acyl group, which may bear one or more pharmaceutically acceptable protecting groups and may be further substituted on the α-nitrogen; and $R^{2c}$ is hydrogen, or $R^{2c}$ is —NR$^a$—CO—($CH_2$)$_m$—$R^b$ or —O—$CH_2$—$R^b$ in which m is 0 or 1, $R^a$ is hydrogen or methyl, and $R^b$ is a ring of formula XII or formula XIII

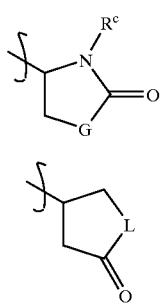

XII

XIII in which G is O, S, NH or $CH_2$ and $R^c$ is hydrogen or methyl, and L is NR$^f$ or $CH_2$ and $R^f$ is hydrogen or methyl; or $R^{2c}$ is —NHCOR$^g$ in which $R^g$ is a five-membered heteroaromatic ring having 2 heteroatoms selected from O, S and N and in which the carbonyl group is bonded to a ring carbon situated between a ring heteroatom and another ring carbon; or $R^{2c}$ is —($CH_2$)$_n$—$R^h$, —O—($CH_2$)$_n$—$R^h$ or —NH—($CH_2$)$_n$—$R^h$ in which n is 0, 1 or 2 and $R^h$ is cyclopentyl, cyano, or —CONR$^i$R$^j$ in which $R^i$ and $R^j$ are independently hydrogen or methyl or the group NR$^i$R$^j$ is pyrrolidino, piperidino, or morpholino; or $R^{2c}$ is —$X^2$—($CH_2$)$_p$—$R^k$, or —O—$CH_2$—CH($CH_3$)—$R^k$ in which $X^2$ is a direct bond, methylene or O and p is 1, 2 or 3, provided that when p is 1, then $X^2$ is a direct bond, and $R^k$ is 2-oxopyrrolidin-1-yl or NHCOR$^m$ in which $R^m$ is (1–3C)alkyl, phenyl or pyridyl; or $R^{2c}$ is —NH—CO—NR$^i$R$^j$ in which $R^i$ and $R^j$ are independently hydrogen or methyl or the group NR$^i$R$^j$ is pyrrolidino, piperidino, or morpholino; or $R^{2c}$ is —O—CO—NR$^p$R$^q$ in which $R^p$ and $R^q$ are independently hydrogen, methyl or ethyl or the group NR$^p$R$^q$ is pyrrolidino, piperidino, or morpholino; or $R^{2c}$ is —NH—$SO_2$—R$^r$ in which R$^r$ is (1–3C)alkyl or phenyl; and provided that either $R^1$ is $R^{1b}$ or $R^2$ is $R^{2b}$.

The α-amino acyl group —CO—A conveniently may be represented as —CO—CH($R^b$)—NR$^f$R$^g$, or may be denoted by standard amino acid nomenclature. Thus, —CO—A may be an α-amino acyl group derived from an α-amino acid selected from glycine, alanine, valine, leucine, isoleucine, phenylalanine, tyrosine, serine, threonine, methionine, cysteine, proline, azetidine-2-carboxylic acid, pipecolic acid, aspartic acid, asparginine, glutamic acid, glutamine, lysine, arginine, histidine, etc. in which an amino group may bear, for example, a t-butoxycarbonyl protecting group; a carboxy group may be protected as its (1–4C)alkyl ester; a hydroxy group may bear, for example, a benzyl protecting group; and a thiol group may bear, for example, a t-butyl protecting group. In addition, when —CO—A is represented as —CO—CH($R^b$)—NR$^f$R$^g$, each of $R^f$ and $R^g$ may be hydrogen or methyl, or —NR$^f$R$^g$ may be a pyrrolidino, piperidino, morpholino or 1,1-dioxothiomorpholin-4-yl group (and $R^b$ denotes the side chain or protected side chain of an α-amino acyl group as defined above).

A particular compound of formula I is a compound of formula Ia

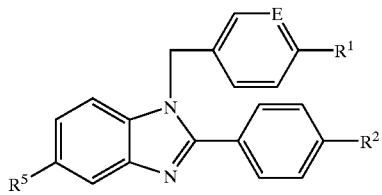

Ia wherein

E is CH or CR$^e$ in which R$^e$ is methyl, methoxy or halo;

$R^1$ is —$X^1$—($CH_2$)$_s$—NR$^s$R$^t$ in which $X^1$ is a direct bond, methylene or O; s is 1 or 2; provided that when s is 1, then $X^1$ is a direct bond; and R$^s$ and R$^t$ are independently hydrogen or (1–3C)alkyl or the group NR$^s$R$^t$ is pyrrolidino, piperidino, morpholino, 1-imidazolyl, 1-pyrazolyl, 1,2,4-triazol-1-yl, or benzylamino;

$R^2$ is hydrogen or —$X^2$—($CH_2$)$_m$—NR$^a$R$^b$ in which $X^2$ is a direct bond, methylene, O or S; m is 1, 2, 3, 4 or 5; provided that when m is 1, then $X^2$ is a direct bond; and $R^a$ and $R^b$ are independently hydrogen or (1–3C)alkyl or the group NR$^a$R$^b$ is pyrrolidino, piperidino, morpholino, 1-imidazolyl, 1-pyrazolyl, 1,2,4-triazol-4-yl, or 2-oxopyrrolidin-1-yl; and $R^5$ is hydrogen, hydroxy or methoxy.

A particular value for —$X^1$—($CH_2$)$_s$—NR$^s$R$^t$ is —$CH_2$—NR$^s$R$^t$ in which NR$^s$R$^t$ is pyrrolidino, 1-imidazolyl, 1-pyrazolyl, 1,2,4-triazol-1-yl, or benzylamino or is —O—($CH_2$)$_2$—NR$^s$R$^t$ in which NR$^s$R$^t$ is pyrrolidino, and more particularly, is —$CH_2$—NR$^s$R$^t$.

A particular value for $R^2$ is —O—($CH_2$)$_2$—NR$^a$R$^b$ in which NR$^a$R$^b$ is pyrrolidino, 1-pyrazolyl or 2-oxopyrrolidin-1-yl. A particular value for $R^5$ is hydroxy.

The present invention also provides a method of inhibiting coagulation in a mammal comprising administering to a mammal in need of treatment, a coagulation inhibiting dose of a thrombin inhibiting compound of formula I having any of the above definitions.

The present invention further provides a method of inhibiting thrombin comprising administering to a mammal in need of treatment, a thrombin inhibiting dose of a thrombin inhibiting compound of formula I having any of the above definitions.

Further, the present invention provides a method of treating a thromboembolic disorder comprising administering to a mammal in need of treatment, an effective dose of a thrombin inhibiting compound of formula I having any of the above definitions.

In addition, there is provided the use of a thrombin inhibiting compound of formula I having any of the above definitions for the manufacture of a medicament for treatment of a thromboembolic disorder.

As a further aspect of the invention, there is provided a prodrug (or a pharmaceutically acceptable salt thereof) of any of the above described thrombin inhibiting compounds of formula I which will form a prodrug. (It will be recognized that a thrombin inhibiting compound of formula I also may serve as a prodrug for a different thrombin inhibiting compound of formula I).

As an additional feature of the invention there is provided a pharmaceutical formulation comprising in association with a pharmaceutically acceptable carrier, diluent or excipient, a prodrug of a thrombin inhibiting compound of formula I (or of a pharmaceutically acceptable salt thereof) as provided in any of the above descriptions.

In general, the thrombin inhibiting compounds of formula I are believed to be novel and, thus, to constitute an additional aspect of the invention. Thus, according to the invention there is provided a novel compound of formula I (or a pharmaceutically acceptable salt thereof) according to any of the above definitions of a compound of formula I, provided that the compound is not one which is not novel A pharmaceutically acceptable salt of an antithrombotic agent of the instant invention includes one which is an acid-addition salt made with an acid which provides a pharmaceutically acceptable anion or one which is a salt made with a base which provides a pharmaceutically acceptable anion. Examples of such acids are provided hereinbelow. Thus, a pharmaceutically acceptable salt of a novel compound of formula I as defined above provides a particular aspect of the invention.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the above descriptions.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

It will be appreciated that certain compounds of formula I (or salts or prodrugs, etc.) may exist in, and be isolated in, isomeric forms, including cis- or trans-isomers, as well as optically active, racemic, or diastereomeric forms. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against thrombin, it being well known in the art how to prepare or isolate particular forms and how to determine inhibitory properties against thrombin by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

A particular value for a (1–2C)alkyl group is methyl or ethyl; for a (1–3C)alkyl group is methyl, ethyl, propyl or isopropyl; for a (1–4C)alkyl group is methyl, ethyl, propyl, isopropyl or butyl; for a (1–5C)alkyl group is methyl, ethyl, propyl, isopropyl, butyl or pentyl; and for a (1–4C)alkoxy group is methoxy, ethoxy, isopropoxy or t-butoxy.

A compound of formula I may be made by processes which include processes known in the chemical art for the production of known compounds of formula I or of structurally analogous compounds or by a novel process described herein. A process for a novel compound of formula I (or a pharmaceutically acceptable salt thereof), novel processes for a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

In general, a compound of formula I may be prepared according to one of the routes outlined in Scheme I, illustrating the preparation of a compound of formula I in which there is a group Q at the 5-position, and described in the examples, in which each of Q, $Q^2$, $Q^3$ and $Q^5$, respectively, represents a value defined for the groups Q, $R^2$, $R^3$ and $R^5$, a protected version of such a group, or moiety which can be further elaborated into such a group. Final conversion of a group Q, $Q^2$, $Q^3$ or $Q^5$ into R, $R^2$, $R^3$ or $R^5$ is carried out at a convenient point, consistent with the chemistry employed.

Scheme I

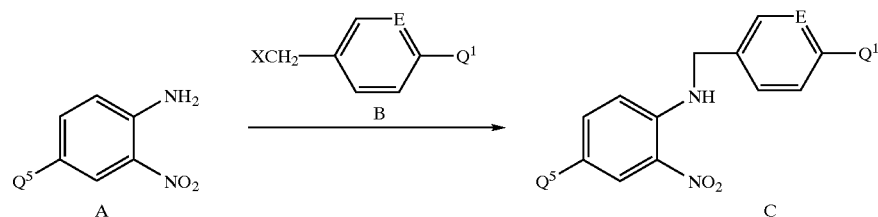

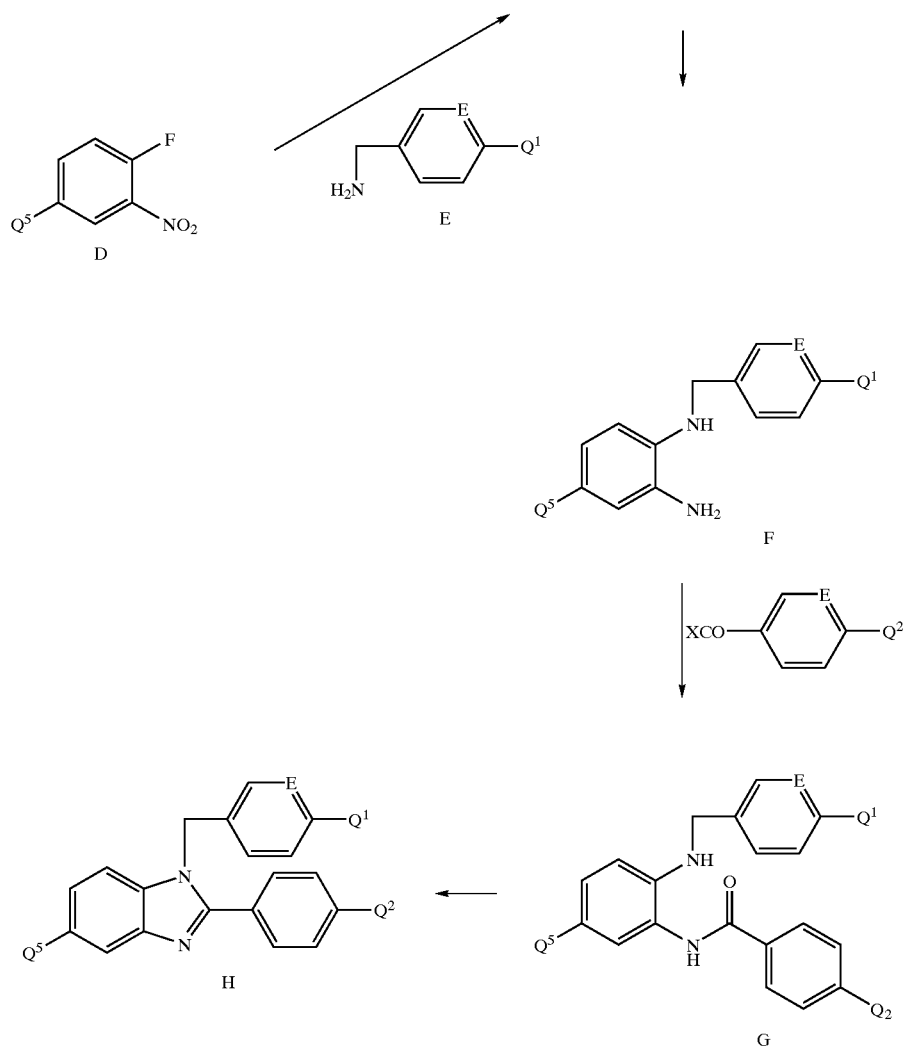

Thus, there is provided a process for preparing a novel compound of formula I (or a pharmaceutically acceptable salt thereof) as provided in any of the above descriptions which is selected from any of those described in the examples, including, cyclizing a corresponding amide of formula II

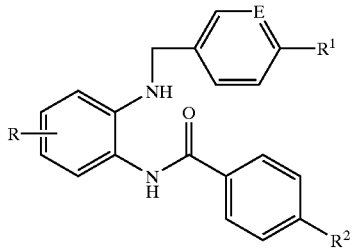

(or for a compound of formula Ia, a compound of formula IIa)

by heating it, for example in an inert solvent as described in the Examples below;

whereafter, for any of the above procedures, when a functional group is protected using a protecting group, removing the protecting group;

whereafter, for any of the above procedures, when a pharmaceutically acceptable salt of a compound of formula I is required, it may be obtained by reacting the basic or acidic form of such a compound of formula I with an acid or base affording a physiologically acceptable counterion or by any other conventional procedure.

Novel intermediate or starting material compounds, such as an amide of formula II provide a further aspect of the invention.

As mentioned above, a compound corresponding to a compound of formula I but in which a functional group is protected may serve as an intermediate for a compound of formula I. Accordingly, such protected intermediates for a novel compound of formula I provide further aspects of the invention. Thus, as one particular aspect of the invention, there is provided a compound corresponding to a novel compound of formula I as defined above in which R (for example as $R^5$) is hydroxy, but in which the corresponding substituent is —$OR^P$ in place of hydroxy, wherein $R^P$ is a phenol protecting group other than methyl. Phenol protecting groups are well known in the art, for example as described in T. W. Greene and P. G. M. Wuts, "Protecting Groups in Organic Synthesis" (1991). Particular values of $R^P$ include, for example, benzyl and allyl. Further, $R^P$ may denote a functionalized resin, for example as disclosed in H. V. Meyers, et al., *Molecular Diversity*, (1995), 1, 13–20.

As mentioned above, the invention includes pharmaceutically acceptable salts of the thrombin inhibiting compounds defined by the above formula I. A particular compound of this invention which possesses one or more sufficiently basic functional groups will react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

A compound of formula I which is acidic forms salts with pharmaceutically acceptable bases. Such a pharmaceutically acceptable salt may be made with a base which affords a pharmaceutically acceptable cation, which includes alkalai metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine. The potassium and sodium salt forms are particularly preferred.

If not commercially available, the necessary starting materials for the preparation of a compound of formula I may be prepared by procedures which are selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of protection and deprotection are well known in the art for preparation of compounds such as those of formula I discussed above.

Generally, the compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions,* John Wiley & Sons, 1981.

The compounds of the invention are believed to selectively inhibit thrombin over other proceinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin in mammals comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment an effective (coagulation inhibiting) dose of a compound of formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally, parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a novel compound of formula I or a pharmaceutically acceptable salt or solvate thereof in association with a pharmaceutically acceptable carrier, diluent or excipient therefor.

The active ingredient in such formulations comprises from 0.1 percent to 9.9 percent by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to formula I or a pharmaceutically acceptable salt or solvate thereof.

Formulation 1:
Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2:
A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3:
An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4:
Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5:
Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6:
Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7:
Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8:
An intravenous formulation may be prepared as follows:

| Active ingredient | 100 mg |
| --- | --- |
| Isotonic saline | 1,000 mL |

The solution of the above ingredients generally is administered intravenously to a subject at a rate of 1 mL per minute.

The ability of the compounds of the present invention to be an effective and orally active thrombin inhibitor are evaluated in one or more of the following assays.

The compounds provided by the invention (formula I) selectively inhibit the action of thrombin in mammals. The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-L-Phe-L-Val-L-Arg-p-nitroanilide.

The assay is carried out by mixing 50 µL buffer (0.03M Tris, 0.15M NaCl, pH 7.4) with 25 µL of human thrombin solution (purified human thrombin, Enzyme Research Laboratories, South Bend, Ind., at 8 NIH units/mL) and 25 µL of test compound in a solvent (50% aqueous methanol (v:v)). Then 150 µL of an aqueous solution of the chromogenic substate (at 0.25 mg/mL) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

$$\text{Thrombin} + I \rightleftharpoons \text{Thrombin} - I$$

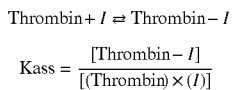

$$\text{Kass} = \frac{[\text{Thrombin} - I]}{[(\text{Thrombin}) \times (I)]}$$

Kass is calculated for a range of concentrations of test compounds and the mean value reported in units of liter per mole. In general, a thrombin inhibiting compound of formula I of the instant invention exhibits a Kass of $0.05 \times 10^6$ L/mole or much greater.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from Kabi Vitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., J. Biol. Chem., 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, Biochem. J., 185, 1–11 (1980); and Smith, et al., Biochemistry, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., Biochemistry, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 µL thrombin (73 NIH unit/mL) to 100 µL human plasma which contains 0.0229 µCi 125-iodine labeled fibrinogen. Clot lysis is studied by overlaying the clots with 50 µL of urokinase or streptokinase (50, 100, or 1000 unit/mL) and incubating for 20 hours at room temperature. After incubation the tubes are centrifuged in a Beckman Microfuge. 25 µL of supernate is added into 1.0 mL volume of 0.03 M tris/0.15 M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 µg/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods
Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982). In this model preferred compounds of the instant invention reduce the net clot weight to approximately 25–30% of control, or even lower, at an i.v. dose of 33.176 $\mu$mol/kg/h.

$FeCl_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 $\mu$L is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.*, 60:269, 1990).

Spontaneous Thrombolysis Model

In vitro data suggests that thrombin inhibitors inhibit thrombin and, at higher concentrations, may inhibit other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and $^{125}I$ human Fibrogen (5 $\mu$Ci, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected cpm} - \text{lung cpm})}{\text{injected cpm}} \times 100$$

The fibrinolytic dissolution of the implanted clot occurs time-dependently (see J. P. Clozel, *Cardiovas. Pharmacol.*, 12:520, 1988).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and $CaCl_2$ (0.1 mL, 0.025 M) is added to start coagulation. Assays are done in duplicate and averaged.

Index of Bioavailability

For a measure of bioactivity, plasma thrombin time (TT) serves as a substitute for the assay of parent compound on the assumption that observed increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{\text{AUC po}}{\text{AUC iv}} \times \frac{\text{Dose iv}}{\text{Dose po}} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means +/−SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Butler Farms, Clyde, N.Y., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for at least 30 minutes.

Hematolocry and Template Bleeding Time Determinations

Whole blood cell counts, hemoglobin, and hematocrit values are determined on a 40-$\mu$L sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl

AIBN=azobisisobutyronitrile

Anal.=elemental analysis

Bn or Bzl=benzyl

Bu=butyl n-BuLi=butyllithium
calcd=calculated
DCC=dicyclohexylcarbodiimide
DIBAL-H=diisobutyl aluminum hydride
DMF=dimethylformamide
DMSO=dimethylsulfoxide
Et=ethyl
EtOAc=ethyl acetate
Et$_3$N=triethylamine
Et$_2$O=diethyl ether
EtOH=ethanol
EtSH=ethanethiol
FAB=Fast Atom Bombardment (Mass Spectrascopy)
FDMS=field desorption mass spectrum
Hex=hexanes
HOAt=1-hydroxy-7-azabenzotriazole
HPLC=High Performance Liquid Chromatography
HRMS=high resolution mass spectrum
i-PrOH=isopropanol
IR=Infrared Spectrum
LAH=lithium aluminum hydride
Me=methyl
MeI=methyl iodide
MeOH=methanol
MPLC=Medium Pressure Liquid Chromatography
NBS=N-bromosuccinimide
NMR=Nuclear Magnetic Resonance
Ph=phenyl
PPA=polyphosphoric acid
i-Pr=isopropyl
Rochelle's Salt=potassium sodium tartrate
RPHPLC=Reversed Phase High Performance Liquid Chromatography
SiO$_2$=silica gel
SM=starting material
TBS=tert-butyldimethylsilyl
TEA=triethylamine
Temp.=temperature
TFA=trifluoroacetic acid
THF=tetrahydrofuran
TIPS=triisopropylsilyl
TLC=thin layer chromatography
triflic acid=trifluoromethanesulfonic acid Unless otherwise stated, pH adjustments and work up are with aqueous acid or base solutions. PrepLC indicates preparative liquid chromatography using "Prep Pak (TM)" silica cartridges; radial chromatography indicates preparative chromatography using a "Chromatotron (TM)" instrument.

EXAMPLE 1

Preparation of 5-Hydroxy-1-[3-methoxy-4-[(1,2,4-triazol-1-yl)methyl]benzyl]-2-[4-[2-(1-pyrrolidinyl)ethoxy]-phenyl]benzimidazole Dioxalate

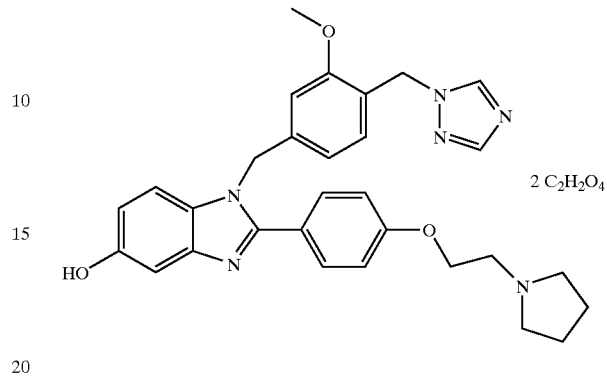

A. 1-[4-(Bromomethyl)-2-methoxyphenyl]-1-propanone

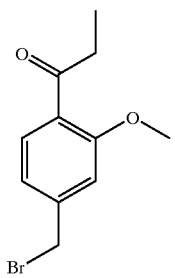

A mixture of 4-methylsalicylic acid (20 g, 131.5 mmol), CH$_3$I (74.7 g, 526.3 mmol), K$_2$CO$_3$ (36.2 g, 262 mmol) and acetone (250 mL) was maintained at reflux for 4 days. After filtering, the filtrate was concentrated under reduced pressure and the resulting residue taken up in Et$_2$O and washed with 2N NaOH. The organic extract was concentrated under reduced pressure. From this crude material, 10 grams (55.6 mmol) was taken up in CCl$_4$ (100 mL) and N-bromosuccinimide (10.8 g, 61.1 mmol) and a catalytic amount of AIBN was added. The mixture was heated at reflux for 4 h and then diluted 10 fold with Et$_2$O. The organics were washed with 25% NaOH (aq.) and concentrated under reduced pressure. Crude product was recrystallized from EtOAc-Hexanes, giving 14.2 g (99%) of the desired bromide.

$^1$H NMR (CDCl$_3$) δ7.77 (d, J=8.3 Hz, 1H), 7.01 (d, J=2.6 Hz, 1H), 6.99 (s, 1H), 4.47 (s, 2H), 3.94 (s, 3H), 3.91(s, 3H).

B. 4-(Dimethyl-t-butylsiloxy)-2-nitroaniline

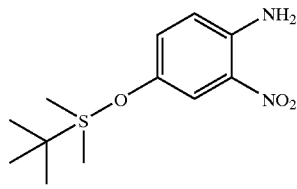

To 4-amino-3-nitrophenol (20 g, 128.9 mmol) was added tert-butyldimethylsilyl chloride (21.5 g, 142.9 mmol), imidazole (13.3 g, 194.8 mmol), and DMF (100 mL). The mixture was stirred at room temperature for 3 h and then diluted with Et$_2$O and washed with H$_2$O. The organics were concentrated under reduced pressure and the resulting solid recrystallized from Et$_2$O—H$_2$O; yielding 26.5 g (76%) product.

$^1$H NMR (CDCl$_3$) δ7.56 (d, J=2.7 Hz, 1H), 6.95 (d, J=3.0 Hz, 1H), 6.70 (d, J=9.0 Hz, 1H), 0.97 (s, 9H), 0.19 (s, 6H); FDMS 268.

C. Methyl 4-[4-(tert-Butyldimethylsilyloxy)-2-nitrophenylamino]methyl-2-methoxybenzoate

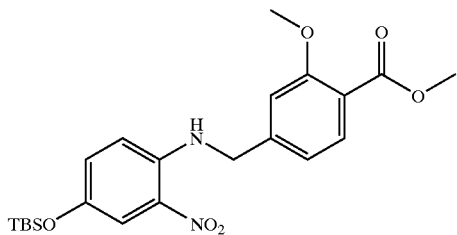

To the bromide (Example 1, Part A; 2.5 g, 9.65 mmol) was added K$_2$CO$_3$ (0.89 g, 6.44 mmol), aniline (Example 1, Part B; 1.72 g, 6.44 mmol), and CH$_3$CN (30 mL). The mixture was heated at 80° C. overnight. After diluting 20 fold with EtOAc, the organics were washed with H$_2$O and concentrated under reduced pressure; yielding 1.5 g (52%) of desired product after flash chromatography (SiO$_2$, 7:1 hexanes-EtOAc).

$^1$H NMR (CDCl$_3$) δ8.2 (s, 1H), 7.8 (d, J=9 Hz, 1H), 7.65 (d, J=4.5 Hz, 1H), 7.05 (d, J=4.5 Hz, 1H), 6.95 (m, 2H), 6.63 (d, J=13.8 Hz, 1H), 4.55 (d, J=9 Hz, 2H), 3.92 (s, 3H), 3.88 (s, 3H), 0.95 (s, 9H), 0.20 (s, 6H); FDMS 446.

D. Methyl 4-[2-Amino-4-(tert-butyldimethylsilyloxy)phenylamino]methyl-2-methoxybenzoate

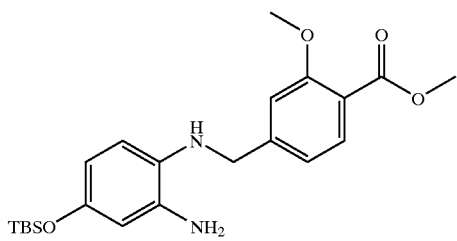

To the above nitro compound (Example 1, Part C; 0.5 g, 1.11 mmol) was added PtO$_2$ (Adam's) catalyst (0.025 g) and EtOH (absolute, 40 mL). The mixture was rapidly stirred under a hydrogen atmosphere (balloon) for 1.5 h and then the catalyst removed by filtering over a pad of diatomaceous earth. The filtrate was concentrated under reduced pressure, yielding 460 mg (99%) of the desired product.

$^1$H NMR (CDCl$_3$) δ7.77 (d, J=8.3 Hz, 1H), 6.99 (d, J=6.8 Hz, 2H), 6.47 (d, J=8.3 Hz, 1H), 6.29 (d, J=2.6 Hz, 1H), 6.22 (dd, J=2.6, 8.3 Hz, 1H), 4.27 (s, 2H), 3.89 (s, 3H), 3.87 (s, 3H), 0.96 (s, 9H), 0.15 (s, 6H); FDMS 416.

E. Methyl 4-[4-(tert-Butyldimethylsilyloxy)-2-[4-[2-(1-pyrrolidinyl)ethoxy]benzoylamino]phenylamino]methyl-2-methoxybenzoate

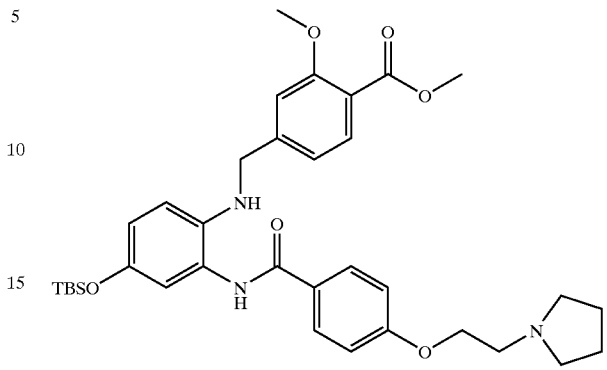

To 4-[2-(1-pyrrolidinyl)ethoxy]benzoic acid (350 mg, 1.29 mmol) in CH$_2$Cl$_2$ (2 ml) was added oxalyl chloride (327 mg, 2.58 mmol) and a catalytic amount of DMF. The mixture was stirred at room temperature for 1 h and then concentrated under reduced pressure. The acid chloride was dried, under vacuum, overnight. To the aniline (Example 1, Part D; 0.49 g, 1.17 mmol), in pyridine (0.158 g, 2.34 mmol) and CH$_2$Cl$_2$ (3 mL) at 0° C. and under N$_2$, was added the previously formed acid chloride (see Example 5, Part D) in 4 mL CH$_2$Cl$_2$ dropwise. Upon completion of addition, the mixture was stirred for 15 minutes at room temperature and then the reaction quenched by the addition saturated NaHCO$_3$. Product was extracted with EtOAc, the organics washed with H$_2$O, and concentrated under reduced pressure; yielding 583 mg of desired product after flash chromatography (SiO$_2$, 10% MeOH in CHCl$_3$).

$^1$H NMR (CDCl$_3$) δ8.31 (s, 1H), 7.81 (d, J=8.7 Hz, 1H), 7.74 (d, J=7.8 Hz, 1H), 7.27 (s, 2H), 6.94 (m, 4H), 6.65 (d, J=8.6 Hz, 1H), 6.57 (dd, J=2.6, 8.5 Hz, 1H), 4.27 (s, 2H), 4.15 (t, J=5.8 Hz, 2H), 3.86 (s, 3H), 3.81 (s, 3H), 2.93 (t, J=5.8 Hz, 2H), 2.65 (s, 4H), 1.83(s, 4H), 0.96 (s, 9H), 0.17 (s, 6H); FDMS 633.

F. 5-(tert-Butyldimethylsilyloxy)-1-(3-methoxy-4-methoxycarbonylbenzyl)-2-[4-[2-(1-pyrrolidinyl)ethoxy]phenyl]-benzimidazole

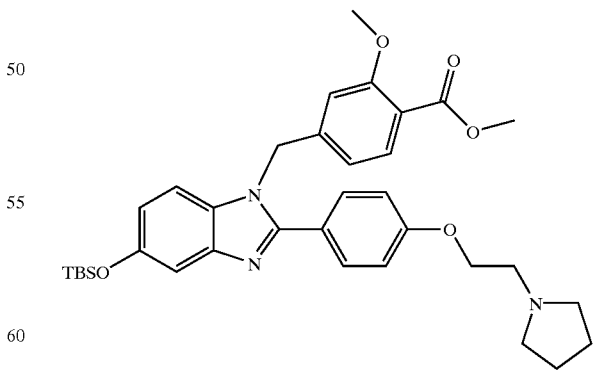

To the above amide (Example 1, Part E; 3.95, 6.23 mmol) was added o-xylene (50 mL) and the mixture heated at reflux overnight. After concentrating under reduced pressure the resulting residue was purified by flash chromatography (SiO$_2$, 5% MeOH in CHCl$_3$ with 1% Et$_3$N v/v added); yielding 3.1 g (82%) of the desired product.

$^1$H NMR (CDCl$_3$) δ7.78 (d, J=7.9 Hz, 1H), 7.58 (d, J=9.0 Hz, 2H), 7.31 (d, J=2.3 Hz, 1H), 6.99 (m, 3H), 6.80 (dd, J=2.26, 8.67 Hz, 1H), 6.76 (d, J=9.4 Hz, 1H), 6.67 (s, 1H), 5.41 (s, 2H), 4.24 (t, J=7.1 Hz, 2H), 3.90 (s, 3H), 3.75 (s, 3H), 3.05 (t, J=7.16 Hz, 2H), 2.78 (s, 4H), 1.89 (s, 4H), 1.02 (s, 9H), 0.23 (s, 6H); FDMS 615.

G. 5-(tert-Butyldimethylsilyloxy)-1-[4-(hydroxymethyl)-3-methoxycarbonylbenzyl]-2-[4-[2-(1-pyrrolidinyl)ethoxy]-phenyl]benzimidazole

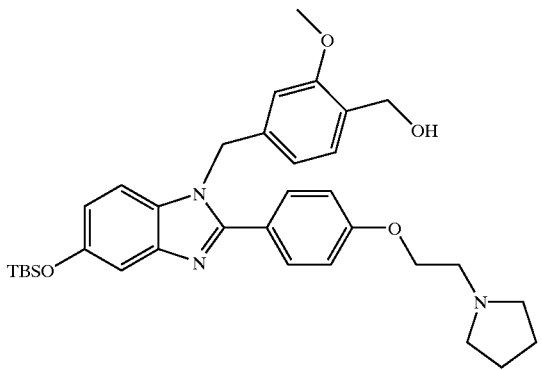

To LAH (31 mg, 0.829 mmol), in THF (10 mL) at 0° C. and under N$_2$, was added the ester (Example 1, Part F; 0.51 g, 0.829 mmol). The mixture was stirred for 25 minutes at 0° C. and then 25 minutes at room temperature. After quenching sequentially with 30 μL H$_2$O, 30 μL of 15% NaOH, and 90 μL of H$_2$O, the mixture was stirred for 1 h and the resulting aluminum salts removed by filtering over a pad of diatomaceous earth, followed by EtOAc washes (3×25 mL). The filtrate was then concentrated under reduce pressure and the resulting residue purified by flash chromatography (SiO$_2$, 10% MeOH in CHCl$_3$); yielding 283 mg (58%) of the desired benzyl alcohol.

$^1$H NMR (CDCl$_3$) δ7.58 (d, J=8.7 Hz, 2H), 7.27 (m, 2H), 6.96 (m, 3H), 6.76 (dd, J=2.3, 6.5 Hz, 1H), 6.67 (d, J=7.6 Hz, 1H), 6.55 (s, 1H), 5.35 (s, 2H), 4.66 (s, 2H), 4.14 (t, J=5.8 Hz, 2H), 3.68 (s, 3H), 2.92 (t, J=5.7 Hz, 2H), 2.65 (s, 4H), 1.81 (s, 4H), 1.01 (s, 9H), 0.23 (s, 6H); FDMS 587.

H. 5-Hydroxy-1-[3-methoxy-4-[(1,2,4-triazol-1-yl)methyl]-benzyl]-2-[4-[2-(1-pyrrolidinyl)ethoxy]phenyl]benzimidazole Dioxalate To the benzyl alcohol (Example 1, Part G; 50 mg, 0.085 mmol) was added CBr$_4$ (42 mg, 0.128 mmol), PPh$_3$ (29 mg, 0.128 mmol) and THF (0.5 mL). The mixture was stirred at room temperature for 45 minutes and then the sodium salt of 1,2,4-triazole (17 mg, 0.255 mmol), in THF (1 mL), was added. The sodium salt of triazole was prepared by adding an equal number of equivalents of NaH (60%) to the triazole in THF and the mixture stirred for 45 minutes. After addition of the triazole, the mixture was stirred for 3 h and then diluted 25 fold with EtOAc. The organics were washed with H$_2$O and concentrated under reduced pressure. The resulting residue was purified by flash chromatography (SiO$_2$, 15% MeOH in CHCl$_3$). This compound was then taken up in TFA (2 mL), allowed to stand for 1 h and then concentrated under reduced pressure. The material was then taken up in EtOAc, 2 equivalents of 0.1 N oxalic acid (in EtOAc) added and the resulting solid collected by centrifugation; yielding 10 mg of a white solid (17%).

$^1$H NMR (CDCl$_3$) δ8.14 (s, 1H), 7.97 (s, 1H), 7.57 (d, J=8.6 Hz, 2H), 7.36 (s, 1H), 7.20 (d, J=7.6 Hz, 1H), 7.01 (d, J=8.6 Hz, 1H), 6.96 (d, J=8.7 Hz, 2H), 6.83 (dd, J=2.0, 8.6 Hz, 1H), 6.73 (d, J=8.4 Hz, 1H), 6.63 (s, 1H), 5.38 (s, 2H), 5.35 (s, 2H), 4.17 (t, J=5.9 Hz, 2H), 3.73 (s, 3H), 2.97 (t, J=5.7 Hz, 2H), 2.71 (s, 4H), 1.87 (s, 4H); FAB MS 525.3 (M+1).

EXAMPLE 2

Preparation of 5-Hydroxy-1-[4-[(1-imidazolyl)methyl]-3-methoxybenzyl]-2-[4-[2-(1-pyrrolidinyl)ethoxy]phenyl]-benzimidazole Dioxalate

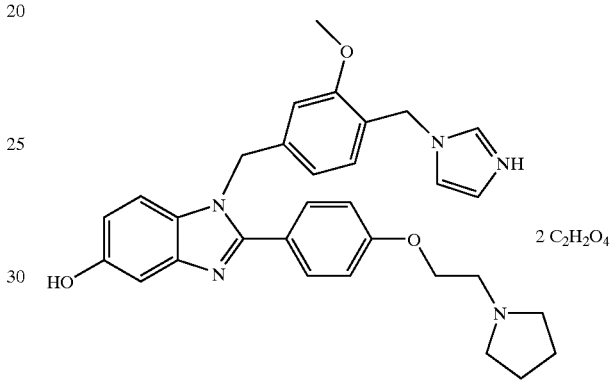

To the benzyl alcohol (Example 1, Part G; 310 mg, 0.528 mmol) was added CBr$_4$ (262 mg, 0.792 mmol), PPh$_3$ (179 mg, 0.792 mmol), and THF (1 mL). The mixture was stirred at room temperature for 1 h and then a mixture of the sodium salt of imidazole (108 mg, 1.58 mmol, in 2.5 mL THF), pre-formed for 1 h from an equimolar amount of NaH in THF, was added. The reaction mixture was stirred at room temperature for 3.5 h and then diluted 25 fold with EtOAc. The organics were washed with H$_2$O and concentrated under reduced pressure. Material was purified by flash chromatography (SiO$_2$, 10% MeOH in CHCl$_3$). To the resulting solid was added 1.0 M TBAF (0.31 mL, 0.314 mmol) and the solution stirred at room temperature for 2.5 h. After diluting 25 fold with EtOAc, the organics were washed with H$_2$O and concentrated under reduced pressure. The resulting residue was purified by flash chromatography (SiO$_2$, 15% MeOH in CHCl$_3$). After taking up the resulting foam in EtOAc (5 mL), the dioxalate salt was formed by adding 2 equivalents of 0.1 N oxalic acid (in EtOAc) and collecting the off-white solid (77 mg, 37%) via centrifugation.

$^1$H NMR (CDCl$_3$) δ7.52 (m, 3H), 7.04 (d, J=6.3 Hz, 2H), 6.92 (m, 6H), 6.59 (s, 2H), 5.29 (s, 2H), 5.04 (s, 2H), 4.21 (t, J=5.2 Hz, 2H), 3.69 (s, 3H), 3.09 (t, J=5.9 Hz, 2H), 2.89 (s, 4H), 1.91 (s, 4H).

EXAMPLE 3

Preparation of 5-Hydroxy-1-[3-methoxy-4-[(1-pyrazolyl)-methyl]benzyl]-2-[4-[2-(1-pyrrolidinyl)ethoxy]phenyl]-benzimidazole Dioxalate

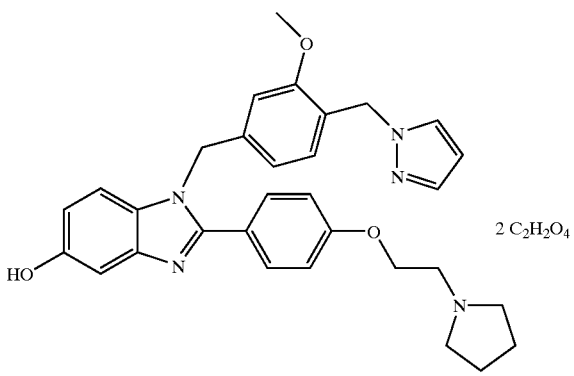

The title compound was prepared in 67% yield from the benzyl alcohol (Example 1, Part G) and the sodium salt of pyrazole by essentially following the procedure detailed in Example 2.

$^1$H NMR (CD$_3$OD) δ7.75 (d, J=8.4 Hz, 2H), 7.62 (d, J=2.0 Hz, 1H), 7.48 (m, 2H), 7.27 (d, J=8.3 Hz, 2H), 7.12 (d, J=1.9 Hz, 1H), 7.05 (d, J=8.4 Hz, 1H), 6.86 (d, J=7.4 Hz, 2H), 6.60 (d, J=8.3 Hz, 1H), 6.28 (s, 1H), 5.66 (s, 2H), 5.29 (s, 2H), 4.46 (s, 2H), 3.78 (s, 3H), 3.70 (bm, 2H), 3.68 (t, J=3.7 Hz, 2H), 3.30 (bm, 2H), 2.10 (s, 4H); FAB MS 524.4 (M+1).

EXAMPLE 4

Preparation of 1-[4-(Benzylamino)methyl-3-methoxybenzyl]-5-hydroxy-2-[4-[2-(1-pyrrolidinyl)ethoxy]phenyl]-benzimidazole Dihydrochloride

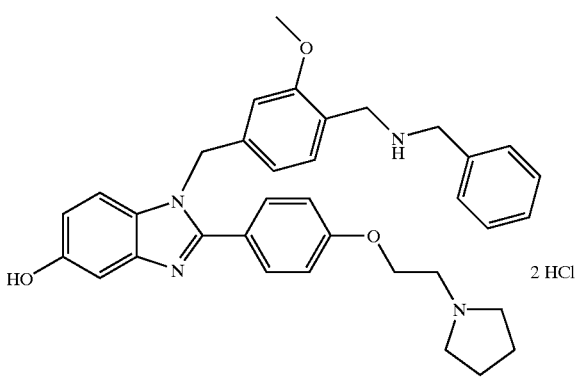

A. 1-[4-(Benzylamino)methyl-3-methoxybenzyl]-5-(tert-butyldimethylsilyloxy)-2-[4-[2-(1-pyrrolidinyl)ethoxy]-phenyl]benzimidazole

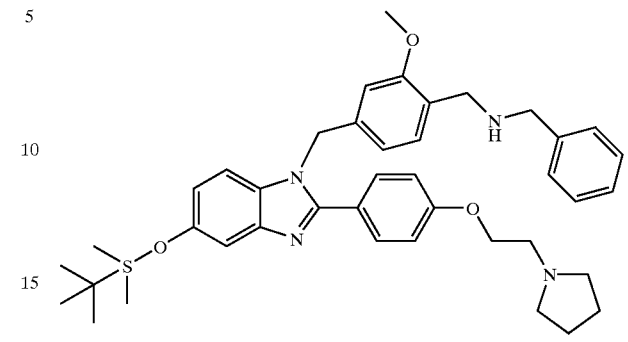

To the benzyl alcohol (Example 1, Part G, 50 mg, 0.085 mmol), was added N-methylmorpholine-N-oxide (15 mg, 0.128 mmol), 4 Å molecular sieves (43 mg, powderized), tetrapropylammonium perruthenate (1.5 mg, 0.05 mmol) and CH$_2$Cl$_2$ (0.25 mL). The mixture was stirred, under N$_2$, for 35 minutes and then diluted 25 fold with EtOAc. The slurry was filtered through a plug of silica gel 60, washing with EtOAc (25 mL) and the filtrate concentrated under reduced pressure. To the resulting aldehyde was added NaCNBH$_3$ (6 mg, 0.091 mmol), 10% HOAc in MeOH (0.28 mL) and benzylamine (18 mg, 0.175 mmol) in MeOH (0.28 mL). The mixture was stirred at room temperature for 1 h and then concentrated under reduced pressure. After taking up the resulting residue in EtOAc (25 mL), the organics were washed with saturated NaHCO$_3$ solution and H$_2$O and concentrated under reduced pressure. The material was purified by flash chromatography (SiO$_2$, 15% MeOH in CHCl$_3$); yielding 22 mg (38%).

$^1$H NMR (CDCl$_3$) δ7.62 (d, J=8.6 Hz, 2H), 7.21–7.35 (m, 7H), 7.03 (d, J=8.6 Hz, 2H), 6.98 (d, J=8.7 Hz, 2H), 6.78 (dd, J=2.1, 8.8 Hz, 1H), 6.68 (d, J=7.5 Hz, 1H), 6.57 (s, 1H), 5.38 (s, 2H), 4.18 (t, J=5.8 Hz, 2H), 3.81 (s, 2H), 3.79 (s, 2H), 3.68 (s, 3H), 2.97 (t, J=5.8 Hz, 2H), 2.69 (s, 4H), 1.85 (s, 4H), 1.01 (s, 9H), 0.23 (s, 6H); FDMS 677.2 (M+1).

B. 1-[4-(Benzylamino)methyl-3-methoxybenzyl]-5-hydroxy-2-[4-[2-(1-pyrrolidinyl)ethoxy]phenyl]benzimidazole Dihydrochloride To the benzyl amine (Example 4, Part A; 20 mg, 0.03 mmol) was added 6 N HCl (1 mL) and the mixture stirred at room temperature for 1 h. The solution was diluted with 5 mL of H$_2$O, washed with Et$_2$O, and the aqueous layer concentrated under reduced pressure; yielding 17 mg (89%) of the desired product.

$^1$H NMR (CD$_3$OD) δ7.83 (d, J=7.8 Hz, 2H), 7.43–7.55 (m, 5H), 7.34 (t, J=5.1 Hz, 3H), 7.15 (d, J=1.9 Hz, 1H), 7.06 (d, J=7.1 Hz, 1H), 7.00 (s, 1H), 6.71 (d, J=7.3 Hz, 1H), 5.76 (s, 2H), 4.51 (s, 2H), 4.22 (s, 2H), 4.14 (s, 2H), 3.83 (s, 3H), 3.73 (s, 4H), 3.28 (s, 2H), 2.07–2.2 (bd, 4H); FAB MS 563.4 (M+1).

EXAMPLE 5

Preparation of 1-[4-[2-(1-Pyrrolidinyl)ethoxy]
benzyl]-2-[4-[2-(1-pyrrolidinyl)ethyoxy]phenyl]
benzimidazole Dioxalate

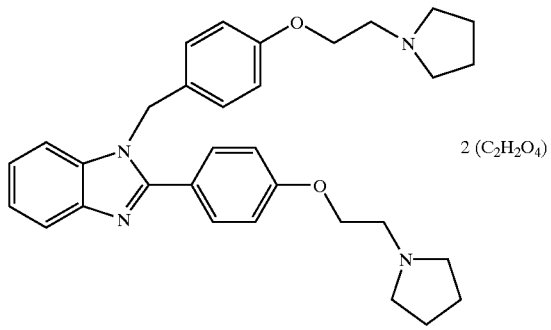

A. Methyl 4-Hydroxybenzoate

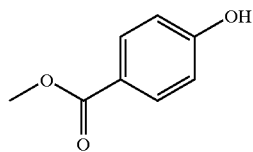

To a solution of 4-hydroxybenzoic acid (138 g, 1.00 mol) in methanol (1000 mL) was added concentrated sulfuric acid (20 mL), then the reaction heated at reflux for 20 h. The reaction mixture was concentrated to one half the original volume under reduced pressure then partitioned with ethyl acetate (1000 mL) and water (1000 mL). The organic layer was washed with 1 N aqueous sodium hydroxide (2×300 mL), water (300 mL), brine (300 mL) then dried (MgSO$_4$). The solvent was removed under reduced pressure to give the ester as a white solid (106.62 g, 70%) after drying under vacuum at ambient temperature.

$^1$HNMR (300 MHz, CDCl$_3$) δ7.98 (d, J=8.6 Hz, 2H), 6.88 (d, J=8.6 Hz, 2H), 5.47 (s, 1H), 3.91 (s, 3H).

B. Methyl 4-[2-(1-Pyrrolidinyl)ethoxy]benzoate

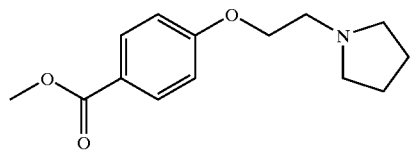

To a solution of methyl 4-hydroxybenzoate (4.56 g, 30 mmol) in dry DMF (60 mL) was added cesium carbonate (31.3 g, 96 mmol, 3.2 eq.) and 1-(2-chloroethyl)pyrrolidine hydrochloride (8.1 g, 48 mmol, 1.6 eq.). The reaction was heated at 80° C. for 20 h. The reaction mixture was cooled to ambient temperature then water (240 mL) was added. The mixture was partitioned with ethyl acetate (250 mL). The aqueous layer was extracted with ethyl acetate (50 mL). The combined extracts were washed with water (240 mL), brine (50 mL), dried (Na$_2$SO$_4$), filtered then concentrated to dryness under reduced pressure. The residue was purified by flash chromatography (90:5:5 hexane:THF:TEA) to give the desired product as an oil (5.3 g, 71%).

$^1$HNMR (300 MHz, CDCl$_3$) δ7.98 (d, J=9.0 Hz, 2H), 6.95 (d, J=9.0 Hz, 2H), 4.19 (t, J=6.0 Hz, 2H), 3.91 (s, 3H), 2.93 (t, J=6.0 Hz, 2H), 2.64 (bm 4H), 1.82 (bm, 4H).

C. 4-[2-(1-Pyrrolidinyl)ethoxy]benzoic Acid Hydrochloride

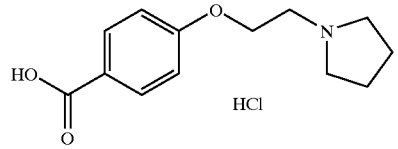

Methyl 4-[2-(1-pyrrolidinyl)ethoxy]benzoate (5.3 g, 21.2 mol) in 1 N aqueous HCl (50 mL) was heated at reflux for 18 h. The reaction mixture was washed with ethyl acetate (2×20 mL). The aqueous solvent was removed under reduced pressure to give the desired acid as a white solid (5.55 g, 96%) after drying under vacuum at ambient temperature.

$^1$HNMR (300 MHz, DMSO-d$_6$) δ7.87 (d, J=8.6 Hz, 2H), 7.05 (d, J=8.6 Hz, 2H), 4.18 (t, J=6.0 Hz, 2H), 3.58 (m, 4H), 3.10 (bm, 2H), 2.00 (bm, 2H), 1.82 (bm, 2H).

D. 4-[2-(1-Pyrrolidinyl)ethoxy]benzamide

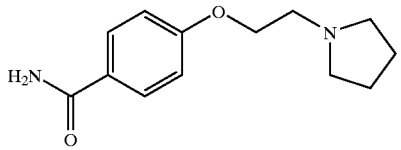

To a suspension of 4-[2-(1-pyrrolidinyl)ethoxy]benzoic acid hydrochloride (750 mg, 2.76 mmol) in dry dichloromethane (10 mL) was added oxalyl chloride (0.481 mL, 5.62 mmol, 2.0 eq.) then a catalytic amount of DMF. After 1 h, the reaction mixture was filtered through a pad of diatomaceous earth, then the solvent was removed under reduced pressure. The residue was treated with excess concentrated ammonium hydroxide in THF (5 mL each). The layers were separated by the addition of brine (10 mL); then the aqueous layer was extracted with THF (2×20 mL). The combined extracts were concentrated to dryness under reduced pressure to give the desired amide as a white solid (602 mg, 93%) after drying under vacuum at ambient temperature.

$^1$HNMR (300 MHz, CDCl$_3$) δ7.78(d, J=9.0 Hz, 2H), 6.95 (d, J=9.0 Hz, 2H), 4.16 (t, J=6.0 Hz, 2H), 2.93 (t, J=6.0 Hz, 2H), 2.64 (bm, 4H), 1.82 (bm, 4H).

E. 4-[2-(1-Pyrrolidinyl)ethoxy]benzyl Amine

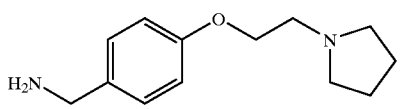

Lithium aluminum hydride (132 mg, 3.49 mmol, 2.1 eq.) was added to a solution of 4-[2-(1-pyrrolidinyl)ethoxy]benzamide (389 mg, 1.66 mmol) in dry THF (25 mL) then the reaction heated at reflux for 20 h. The reaction was allowed to cool to ambient temperature then quenched with water (0.250 mL). Aqueous sodium hydroxide (0.250 mL of 15% w/v) then water (0.750 mL) was added and the reaction stirred for 30 min. The reaction mixture was passed through a pad of diatomaceous earth which was washed with THF (3×15 mL). The combined organics were concentrated under reduced pressure to give the amine as oil (372 mg, >100%) which was used without further purification.

$^1$HNMR (300 MHz, CDCl$_3$) δ7.14 (d, J=9.0 Hz, 2H), 6.82 (d, J=9.0 Hz, 2H), 4.02 (t, J=6.0 Hz, 2H), 3.17 (s, 2H), 2.82 (t, J=6.0 Hz, 2H), 2.55 (bm 4H), 1.74 (bm, 4H).

F. N-[4-[2-(1-Pyrrolidinyl)ethoxy]benzyl]-2-nitroaniline

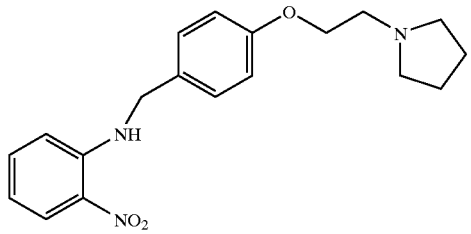

2-Fluoronitrobenzene (0.175 mL, 1.66 mmol, 1.0 eq.), 4-[2-(1-pyrrolidinyl)ethoxy]benzyl amine (366 mg, 1.66 mmol) and anhydrous potassium carbonate (460 mg, 3.32 mmol, 2.0 eq.) were combined in dry THF (16 mL) then allowed to stir 18 h at ambient temperature. The reaction mixture was filtered through a bed of diatomaceous earth, then the solvent was removed under reduced pressure. The crude oil was purified by flash chromatography (eluting with 20:1 CHCl$_3$:MeOH, 0.5% TEA) to give the substituted nitroaniline as a bright yellow oil (252 mg, 44%).

$^1$HNMR (300 MHz, CDCl$_3$) δ8.34 (bs, 1H), 8.17 (d, J=9.0 Hz, 1H), 7.37 (t, J=6.0 Hz, 1H), 7.25 (d, J=9.0 Hz, 2H), 6.91 (d, J=9.0 Hz, 2H), 6.82 (d, J=9.0 Hz, 1H), 6.63, (t, J=9.0 Hz, 1H), 4.45 (d, J=6.0 Hz, 2H), 4.10 (t, J=6.0 Hz, 2H), 2.90 (t, J=6.0 Hz, 2H), 2.63 (bm 4H), 1.80 (bm, 4H); FDMS m/e 342.3 (M+H); FABMS m/e 341.2 (M$^+$).

G. N$^1$-[4-[2-(1-Pyrrolidinyl)ethoxy]benzyl]-1,2-benzenediamine

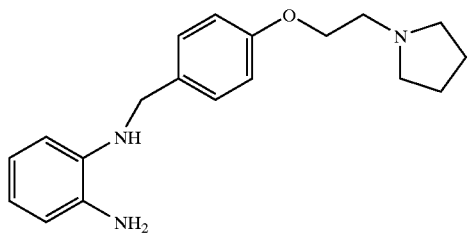

Adam's catalyst (50 mg, 20% wt.), was added to a degassed solution of N-[4-[2-(1-pyrrolidinyl)ethoxy]benzyl]-2-nitroaniline (240 mg, 0.703 mmol) in absolute ethanol (5 mL). The atmosphere was replaced with hydrogen then the reaction was stirred vigorously at ambient temperature until all of the nitro compound had been consumed as determined by tlc (9:1 CHCl$_3$:MeOH, 1% TEA). The reaction mixture was filtered through a bed of diatomaceous earth, then the solvent was removed under reduced pressure to give the desired product as a brown yellow oil (218 mg, 100%).

$^1$HNMR (300 MHz, CDCl$_3$) δ7.30 (d, J=9.0 Hz, 2H), 6.90 (d, J=9.0 Hz, 2H), 6.81 (t, J=9.0 Hz, 1H), 6.75 (m 3H), 4.23 (s, 2H), 4.17 (t, J=6.0 Hz, 2H), 3.00 (t, J=6.0 Hz, 2H), 2.77 (bm 4H), 1.89 (bm, 4H).

H. N$^1$-[4-[2-(1-Pyrrolidinyl)ethoxy]benzyl]-N$^2$-[4-[2-(1-pyrrolidinyl)ethoxy]benzoyl]-1,2-benzenediamine

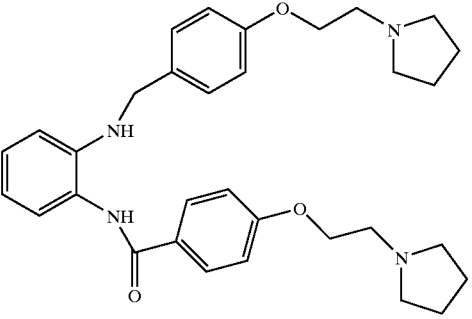

To a solution of N$^1$-[4-[2-(1-pyrrolidinyl)ethoxy]-benzyl]-1,2-benzenediamine (220 mg, 0.706 mmol) in dry dichloromethane (2 mL) was added pyridine (0.114 mL, 1.41 mmol, 2.0 eq.). To the resulting solution was added a suspension of 4-[2-(1-pyrrolidinyl)ethoxy]benzoyl chloride (179 mg, 0.706 mmol, 1.0 eq.) in dry dichloromethane (3 mL), portionwise, at 0° C., following the reaction by tlc (9:1 CHCl$_3$:MeOH, 1% TEA). Once the aniline had been consumed, the reaction was allowed to warm to ambient temperature. The reaction was quenched by the addition of saturated aqueous sodium bicarbonate solution (15 mL) then diluted with ethyl acetate (60 mL). The organic layer was washed with saturated aqueous sodium bicarbonate (15 mL), water (15 mL), brine (15 mL), dried over MgSO$_4$, filtered then the solvent was removed under reduced pressure. The desired product was obtained after flash chromatography (eluting with 20:1 CHCl$_3$:MeOH, 0.5% TEA) as a brown foam (361 mg, 97%).

$^1$HNMR (300 MHz, CDCl$_3$) δ8.57 (bs, 1H), 7.83 (d, J=9.0 Hz, 2H), 7.22 (t, J=9.0 Hz, 1H), 7.18 (d, J=9.0 Hz, 2H), 7.02 (t, J=9.0 Hz, 1H), 6.82 (d, J=9.0 Hz, 2H), 6.75 (d, J=9.0 Hz, 2H), 6.65 (m, 2H), 4.59 (bs, 1H), 4.17 (s, 2H), 4.02 (m, 4H), 2.90 (m, 4H), 2.66 (bm 8H), 1.77 (bm, 8H); FDMS m/e 529 (M+1); FABHRMS cal'c for C$_{32}$H$_{41}$N$_4$O$_3$: 529.3179, found: 529.3170; IR (CHCl$_3$) 2968, 1662, 1607, 1511, 1474, 1458, 1305, 1248, 1176 cm$^{-1}$.

I. 1-[4-[2-(1-Pyrrolidinyl)ethoxy]benzyl]-2-[4-[2-(1-pyrrolidinyl)ethoxy]phenyl]benzimidazole Dioxalate The title compound was prepared by dissolving N$^1$-[4-[2-(1-pyrrolidinyl)ethoxy]benzyl]-N$^2$-[4-[2-(1-pyrrolidinyl)-ethoxy]benzoyl)-1,2-benzenediamine (361 mg, 0.683 mmol) in o-xylene (6 mL) then heating at 150° C., following the reaction by tlc (9:1 CHCl$_3$:MeOH, 1% TEA). Once the amide had been consumed, the reaction was allowed to cool to ambient temperature. The solvent was removed under reduced pressure. The desired product was obtained after flash chromatography (eluting with 20:1 CHCl$_3$:MeOH, 0.5% TEA) to give a glass (218 mg, 62%) after removal of solvent under reduced pressure. The oxalate salt was formed by dissolution in ethyl acetate (1 mL) followed by the addition of a solution of oxalic acid in ethyl acetate (0.426 mL of 0.1 M). The supernatant above the resulting gum was decanted then the gum washed with ethyl acetate (2×1 mL). The gum was triturated with diethyl ether to give a more managable solid (185 mg, 57%).

$^1$HNMR (300 MHz, CD$_3$OD) δ7.75 (d, J=9.0 Hz, 1H), 7.61 (d, J=8.7 Hz, 2H), 7.58 (d, J=9.0 Hz, 1H), 7.41 (d, J=9.0 Hz, 1H), 7.25 (m, 2H), 7.15 (d, J=9.0 Hz, 2H), 6.91 (d, J=9.0 Hz, 2H), 6.88 (d, J=9.0 Hz, 2H), 5.46 (s, 2H), 4.35 (t, J=6.0 Hz, 2H), 4.21 (t, J=6.0 Hz, 2H), 3.53 (m, 4H), 3.32 (bm 8H), 2.02 (bm, 8H); FDMS m/e=511.2 (M+1); FABHRMS cal'c for C$_{32}$H$_{39}$N$_4$O$_2$: 511.3037, found: 511.3067; IR (CHCl$_3$) 2969, 1612, 1513, 1460, 1246 cm$^{-1}$.

EXAMPLE 6

Preparation of 1-[3-Methoxy-4-(1-pyrrolidinyl)methylbenzyl]-2-[4-[2-(1-pyrazolyl)ethoxy]phenyl]benzimidazole Dihydrochloride

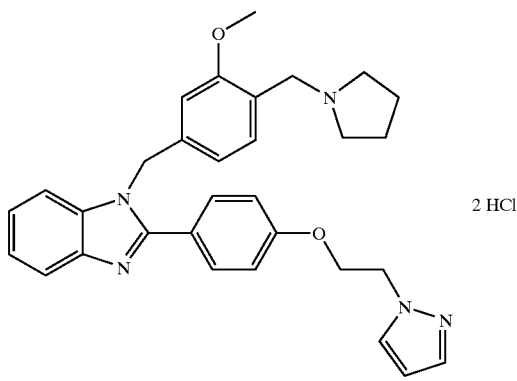

A. 3-Methoxy-4-(1-pyrrolidinyl)methylbenzoic Acid Hydrochloride

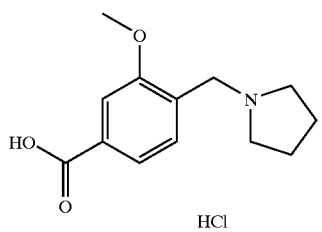

Methyl 3-methoxy-4-[(1-pyrrolidinyl)methyl]benzoate (prepared by bromination of methyl 3-methoxy-4-methylbenzoate by the procedure of Example 1, Part A, followed by treatment with pyrrolidine) (11.56 g, 46.4 mmol), was combined with sodium hydroxide (3.71 g 92.7 mmol, 2.00 eq.) in absolute ethanol (95 mL). After 72 h, the reaction mixture was made acidic to pH 1 by the addition of conc. HCl. The solvent was removed under reduced pressure to give the corresponding acid hydrochloride as a white solid (17.92 g, 99%).

$^1$HNMR (300 MHz, DMSO-d$_6$) δ7.71 (d, J=7.6 Hz, 1H), 7.55 (d, J=7.8 Hz, 1H), 7.54 (s, 1H), 4.33 (s, 2H), 3.89 (s, 3H), 3.35 (bm, 2H), 3.05 (bm, 2H), 1.92 (bm, 4H).

B. 3-Methoxy-4-[(1-pyrrolidinyl)methyl]benzamide

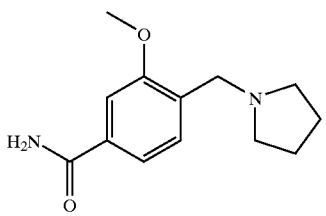

3-Methoxy-4-[(1-pyrrolidinyl)methyl]benzoic acid hydrochloride (15.93 g, 41.1 mmol) was suspended in dichloromethane (200 mL) and a few drops of DMF were added. Oxalyl chloride (676 mg, 58%) was added dropwise then the reaction was allowed to stir for 3 h after the addition was complete. The reaction was filtered through a bed of diatomaceous earth, then the solvent was removed under reduced pressure. The residue was treated with excess concentrated ammonium hydroxide (20 mL) and THF (40 mL). The aqueous layer was saturated with sodium chloride then extracted exhaustively with THF (4×50 mL). The solvent was removed under reduced pressure to give the desired product as a tan solid (11.2 g, 99%).

$^1$HNMR (300 MHz, CHCl$_3$) δ7.48 (d, J=8.7 Hz, 1H), 7.45 (s, 1H), 7.26 (d, J=8.7 Hz, 1H), 6.10 (bs, 1H), 5.65 (bs, 1H), 3.90 (s, 3H), 3.73 (s, 2H), 2.61 (bm, 4H), 1.83 (bm, 4H); IR (CHCl$_3$) 3009, 2968, 2938, 1673, 1585, 1464, 1414, 1365, 1350, 1250, 1107, 1038 cm$^{-1}$; FDMS m/e 234 (M+). Anal. Cal'c for C$_{13}$H$_{18}$N$_2$O$_2$ 1/3 H$_2$O: C, 64.98; H, 7.83; N, 11.66; found: C, 64.92; H, 7.54; N, 11.53.

C. 3-Methoxy-4-[(1-pyrrolidinyl)methyl]benzylamine

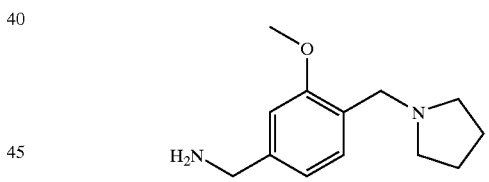

3-Methoxy-4-[(1-pyrrolidinyl)methyl]benzamide (11.2 g, 47.8 mmol) was combined with lithium aluminum hydride (3.8 g 100 mmol, 2.10 eq.) in dry THF (320 mL). The reaction was heated at reflux until all of the starting amide had been consumed by tlc (9:1 CHCl$_3$:MeOH, 1% TEA). The reaction mixture was allowed to cool to room temperature then water (5 mL) slowly was added. After 15 min, aqueous sodium hydroxide (5 mL of 15% w/v) was added followed by more water (15 mL). After 10 min, the reaction mixture was filtered through a pad of diatomaceous earth. The solvent was removed under reduced pressure to give the amine as an amber oil (7.95 g, 76%).

$^1$HNMR (300 MHz, CDCl$_3$) δ7.34 (d, J=7.5 Hz, 1H), 6.90 (d, J=7.8 Hz, 1H), 6.88 (s, 1H), 3.90 (s, 2H), 3.88 (s, 3H), 3.69 (s, 2H), 2.60 (bm, 4H), 1.82 (bm, 4H); FDMS m/e 220.1 (M+); IR(CHC$_3$) 303, 2964, 2937, 2915, 2878, 2804, 1613, 1506, 1464, 1418, 1262, 1109, 1040, 868 cm$^{-1}$.

D. N-[3-Methoxy-4-[(1-pyrrolidinyl)methyl]benzyl]-2-nitroaniline

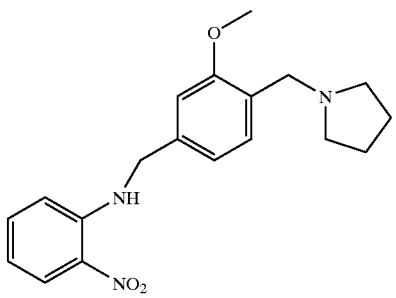

2-Fluoronitrobenzene (0.358 mL, 3.4 mmol, 1.0 eq.), 3-methoxy-4-[(1-pyrrolidinyl)methyl]benzyl amine (750 mg, 3.4 mmol) and anhydrous potassium carbonate (471 mg, 3.4 mmol, 1.0 eq.) were combined in dry THF (35 mL) then allowed to stir 48 h at ambient temperature. The reaction mixture was filtered through a bed of diatomaceous earth then the solvent was removed under reduced pressure. The crude oil was purified by flash chromatography (eluting with 20:1 CHCl$_3$:MeOH, 0.5% TEA) to give the desired product as a right orange oil (676 mg, 58%).

$^1$HNMR (300 MHz, DMSO-d$_6$) δ8.61(t, J=5.5 Hz, 1H), 8.08 (d, J=8.7 Hz, 1H), 7.42 (t, J=8.7 Hz, 1H), 6.95 (s, 1H), 6.94 (d, J=8.7 Hz, 1H), 6.85 (d, J=8.7 Hz, 1H), 6.62 (t, J=5.5 Hz, 1H), 4.58, d, J=5.6 Hz, 2H), 3.75 (s, 3H), 3.57 (s, 2H), 3.38 (bs, 1H), 2.46 (bm, 4H), 1.72 (bm, 4H); IR (CHCl$_3$) 1619, 1575, 1512, 1420, 1266, 1244 cm$^{-1}$; FDMS m/e 341 (M+); FABHRMS cal'c for C$_{19}$H$_{24}$N$_3$O$_3$: 342.1818; found: 342.1815. Anal. Cal'c for C$_{19}$H$_{23}$N$_3$O$_3$ H$_2$O: C, 63.49; H, 7.01; N, 11.69; found: C, 63.25; H, 6.53; N, 11.30.

E. N$^1$-[3-Methoxy-4-[(1-pyrrolidinyl)methyl]benzyl]-1,2-benzenediamine

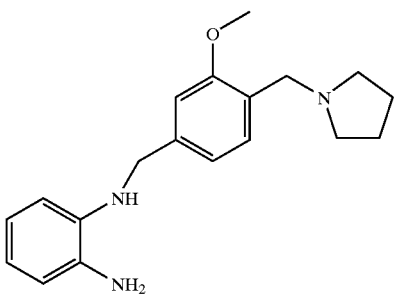

The title compound was prepared by the addition of Adam's catalyst (160 mg, 10% wt.) to a degassed solution of N-[3-methoxy-4-[(1-pyrrolidinyl)methyl]benzyl]-2-nitroaniline (1.6 g, 4.69 mmol) in absolute ethanol (25 mL). The atmosphere was replaced with hydrogen then the reaction was stirred vigourously at ambient temperature until all of the nitro compound had been consumed as determined by tlc (9:1 CHCl$_3$:MeOH, 1% TEA). The reaction mixture was filtered through a bed of diatomaceous earth, then the solvent was removed under reduced pressure to give the diamine as a brown yellow oil (1.46 g, 100%).

$^1$HNMR (300 MHz, CDCl$_3$) d 7.35 (d, J=9.0 Hz, 1H), 7.00 (d, J=9.0 Hz, 1H), 6.93 (s, 1H), 6.85–6.64 (m 4H), 4.30 (s, 2H), 3.83 (s, 3H), 3.74 (s, 2H), 2.77 (bm 4H), 1.89 (bm, 4H).

F. Methyl 4-(2-Bromoethoxy)benzoate

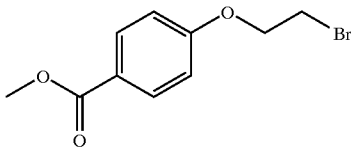

Methyl 4-hydroxybenzoate (5.0 g, 32.86 mmol) was combined with 1,2-dibromoethane (35 mL) and potassium carbonate (6.8 g, 49.23 mmol, 1.5 eq.) then heated at reflux for 18 h. The reaction mixture was concentrated under reduced pressure then the residue partitioned between ethyl ether (500 mL) and water (200 mL). The ether was extracted with 2 N sodium hydroxide (5×50 mL). The solvent was removed under reduced pressure to give the desired product as a white solid (8.47 g, 99%).

$^1$HNMR (300 MHz, CHCl$_3$) δ8.00 (d, J=9.0 Hz, 2H), 6.93 (d, J=9.0 Hz, 2H), 4.35 (t, J=6.0 Hz, 2H), 3.90 (s, 3H), 3.66 (t, J=6.0 Hz, 2H).

G. 4-[2-(1-Pyrazolyl)ethoxy]benzoic Acid Hydrochloride

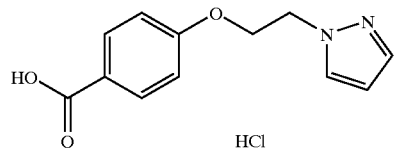

Pyrazole (788 mg, 11.6 mmol, 3.0 eq) was added to a suspension of sodium hydride (463 mg of 60% w/w, 11.6 mmol, 3.0 eq.) in THF (10 mL). After 1 h, the suspension of the sodium salt of pyrazole thus formed was added to a solution of methyl 4-(2-bromoethoxy)benzoate (1.0 g, 3.86 mmol) and a catalytic amount of tetrabutylammonium iodide in dry THF (10 mL) The reaction was heated at reflux for 18 h. The reaction mixture was concentrated under reduced pressure before the residue was partitioned between ethyl acetate (150 mL) and 2 N sodium hydroxide (50 mL). The aqueous layer was made acidic to pH 3 with conc. HCl, and the resulting solid was collected via suction filtration, then air dried to give the acid as a white solid (690 mg, 77%).

¹HNMR (300 MHz, DMSO-d₆) δ7.83 (d, J=9.0 Hz, 2H), 7.75 (d, J=1.7 Hz, 1H), 7.43 (d, J=1.7 Hz, 1H), 6.95 (d, J=9.0 Hz, 2H), 6. 21 (t, J=1.7 Hz, 1H), 4.48 (t, J=6.0 Hz, 2H), 4.37 (t, J=6.0 Hz, 2H).

B. N¹-[3-Methoxy-4-[(1-pyrrolidinyl)methyl]benzyl]-N²-[4-[2-(1-pyrazolyl)ethoxy]benzoyl]-1,2-benzenediamine

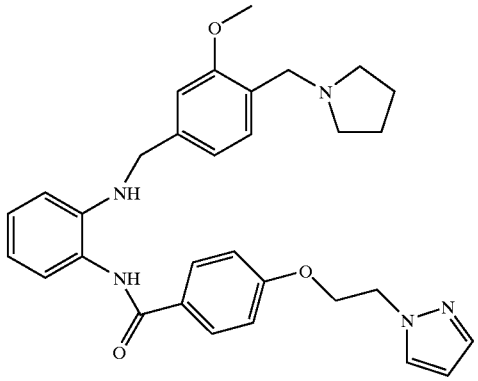

3-Methoxy-4-[(1-pyrrolidinyl)methyl]benzoic acid hydrochloride (250 mg, 1.08 mmol) was suspended in dichloromethane (10 mL), and a drop of DMF was added. Oxalyl chloride (0.197 mL, 2.26 mmol, 2.1 eq) was added dropwise then the reaction was allowed to stir for 2 h after the addition was complete. The reaction was filtered through a bed of diatomaceous earth, then the solvent was removed under reduced pressure. The title compound was prepared from N¹-[3-methoxy-4-[(1-pyrrolidinyl)methyl]-benzyl]-1,2-benzenediamine (Part E above) and the acid chloride described above in 56% yield by following essentially the same procedure as that for Example 5, Part H.

¹HNMR (300 MHz, CDCl₃) δ8.82 (bs, 1H), 7.94 (d, J=8.4 Hz, 2H), 7.51 (d, J=1.8 Hz, 1H), 7.50 (d, J=1.8 Hz, 1H), 7.39 (d, J=7.7 Hz, 1H), 7.24 (d, J=7.7 Hz, 1H), 7.03 (t, J=7.5 Hz, 1H), 6.99 (s, 1H), 6.90 (d, J=7.5 Hz, 1H), 6.82 (d, J=8.7 Hz, 2H), 6.67 (t, J=7.7 Hz, 1H), 6.60 (d, J=8.1 Hz, 1H), 6.23 (t, J=1.5 Hz, 1H), 4.90 (bs, 1H), 4.49 (t, J=5.1 Hz, 2H), 4.30 (m, 4H), 4.05 (s, 2H), 3.75 (s, 3H), 3.12 (bm, 4H), 1.94 (bm 4H).

I. 1-[3-Methoxy-4-[(1-pyrrolidinyl)methyl]benzyl]-2-[4-[2-(1-pyrazolyl)ethoxy]phenyl]benzimidazole Dihydrochloride The title compound was prepared by dissolution of N¹-[3-methoxy-4-[(1-pyrrolidinyl)methyl]benzyl]-N²-[4-[2-(1-pyrazolyl)ethoxy]benzoyl]-1,2-benzenediamine (67 mg, 0.127 mmol) in o-xylene (10 mL) then heating at 150° C. for 18 h. The reaction was allowed to cool to ambient temperature, the solvent was removed under reduced pressure. The residue was passed through a plug of silica gel with 30:1 CHCl₃:MeOH, 0.5% TEA to remove non-polar impurities. The residue was purified by preparative reversed-phase HPLC to give the title compound as the dihydrochloride salt (11 mg, 15%).

¹HNMR (300 MHz, CD₃OD) δ8.15 (s, 1H), 7.98 (s, 1H), 7.88 (d, J=8.0 Hz, 2H), 7.83–7.78 (m, 2H), 7.77–7.59 (m, 2H), 7.41 (d, J=6.9 Hz, 1H), 7.26 (d, J=7.2 Hz, 2H), 7.03 (s, 1H), 6.73 (d, J=6.9 Hz, 1H), 6.60 (s, 1H), 5.82 (s, 2H), 4.81 (d, J=6.0, 2H), 4.54 (t, J=6.0 Hz, 2H), 4.34 (s, 2H), 3.86 (s, 3H), 3.46 (bm 2H), 3.17 (bm, 2H), 2.15 (bm, 2H), 2.02 (bm, 2H); FDMS m/e 508 (M+H).

EXAMPLE 7

Preparation of 1-[3-Methoxy-4-[(1-pyrrolidinyl)methyl]-benzyl]-2-[4-[2-(2-oxopyrrolidin-1-yl)ethoxy]phenyl]-benzimidazole Oxalate

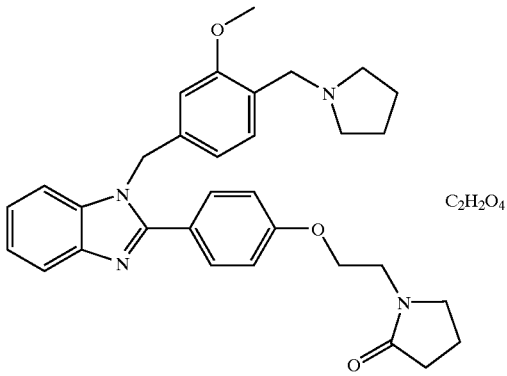

A. 4-[2-(2-Oxopyrrolidin-1-yl)ethoxy]benzoic Acid

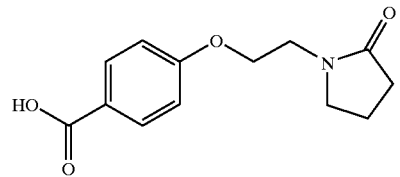

2-Pyrrolidinone (0.859 mL, 11.3 mmol, 2.6 eq) was added to a suspension of sodium hydride (452 mg of 60% w/w, 11.3 mmol, 2.6 eq.) in THF (10 mL). After 1 h, the suspension of the sodium salt of 2-pyrrolidinone thus formed was added to a solution of methyl 4-(2-bromoethoxy)benzoate (1.17 g, 4.52 mmol) and a catalytic amount of tetrabutylammonium iodide in dry THF (10 mL). The reaction was heated at reflux for 18 h. The reaction mixture was concentrated under reduced pressure then the residue partitioned between ethyl acetate (150 mL) and 2 N sodium hydroxide (50 mL). The aqueous layer was made acidic to pH 3 with conc. HCl; then the solvent was removed under reduced pressure. The resulting solid was triturated with ethyl acetate to give the acid as a white solid (523 mg, 46%).

¹HNMR (300 MHz, DMSO-d₆ δ7.90 (d, J=9.0 Hz, 2H), 7.01 (d, J=9.0 Hz, 2H), 4.18 (t, J=6.0 Hz, 2H), 3.58 (t, J=6.0 Hz, 2H), 3.41(t, J=8.0 Hz, 2H), 3.26 (bs, 1H), 2.21 (t, J=8.0 Hz, 2H) 4.18 (q, J=8.0 Hz, 2H).

39

B. N¹-[3-Methoxy-4-[(1-pyrrolidinyl)methyl]
benzyl]-N²-[4-[2-(2-oxopyrrolidin-1-yl)ethoxy]
benzoyl]-1,2-benzenediamine

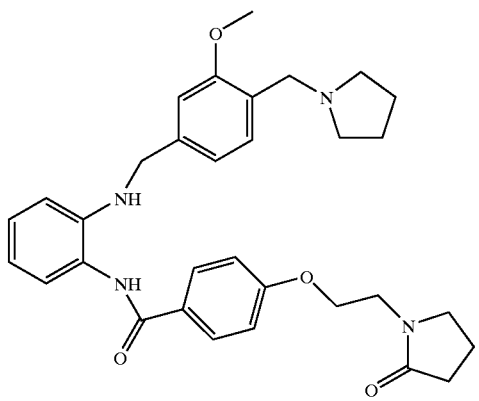

To a suspension of 4-[2-(2-oxopyrrolidin-1-yl)ethoxy]-benzoic acid (250 mg, 1.0 mmol) in dry dichloromethane (10 mL) was added oxalyl chloride (0.184 mL, 2.1 mmol, 2.1 eq.) then a catalytic amount of DMF. After 1 h, the solvent was removed under reduced pressure. The residue was suspended in dry dichloromethane (9 mL) then added portionwise to a ) solution of N¹-[3-methoxy-4-[(1-pyrrolidinyl)methyl]benzyl]-1,2-benzenediamine (prepared according to Example 6, Part E) (292 mg, 0.94 mmol, 0.94 eq.) in dry dichloromethane (1 mL) and pyridine (0.182 mL, 2.25 mmol, 2.25 eq.) at 0° C. until all of the aniline had been consumed by tlc (9:1 CHCl₃:MeOH). The reaction mixture was allowed to warm to ambient temperature then quenched with the addition of a saturated aqueous solution of sodium bicarbonate (10 mL). The reaction mixture was diluted with ethyl acetate (50 mL) then the layers were separated. The organic layer was dried (MgSO₄), filtered, then concentrated under reduced pressure. The amide was obtained as a tan foam (140 mg, 26%) after flash chromatography (2–10% MeOH, 0.5% TEA in CHCl₃).

¹HNMR (300 MHz, CDCl₃) δ8.20 (bs, 1H), 7.95 (d, J=9.0 Hz, 2H), 7.59 (d, J=8.7 Hz, 1H), 7.39–7.25 (m, 2H), 7.15 (t, J=8.7 Hz, 1H), 7.05 (d, J=9.0 Hz, 2H), 6.98 (d, J=9.0 Hz, 2H), 6.81 (t, J=8.7 Hz, 1H), 6.72 (d, 8.7 Hz, 1H), 4.80 (bs, 1H), 4.42 (s, 2H), 4.21(t, J=5.9 Hz, 2H), 3.82 (s, 3H), 3.75 (t, J=6.0 Hz, 2H), 3.61 (t, J=5.9 Hz, 2H), 3.10 (bm, 4H), 2.41 (t, J=5.9 Hz, 2H), 2.05 (bm, 6H).

C. 1-[3-Methoxy-4-[(1-pyrrolidinyl)methyl]benzyl]-
2-[4-[2-(2-oxopyrrolidin-1-yl)]ethoxy]phenyl]
benzimidazole Dioxalate The title compound was prepared from 1,2-N-[3-methoxy-4-[(1-pyrrolidinyl)methyl]benzyl]-N'-[4-[2-(2-oxopyrrolidin-1-yl)ethoxy]benzoyl]phenylene diamine in 35% yield by following essentially the same procedure as for Example 5, Part I.

FDMS m/e=525 (M+H).

40

EXAMPLE 8

Preparation of 1-[3-Methoxy-4-[(1-pyrrolidinyl)-
methyl]benzyl]-2-phenylbenzimidazole Dioxalate

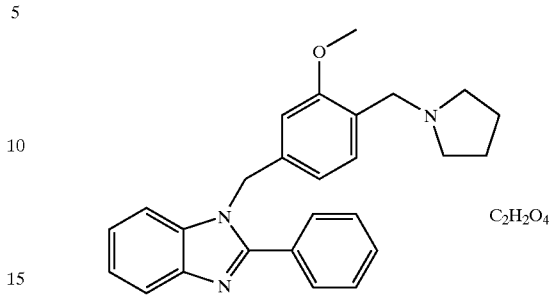

To a solution of N¹-[3-methoxy-4-[(1-pyrrolidinyl)-methyl]benzyl]-1,2-benzenediamine (100 mg, 0.32 mmol) in dry dichloromethane (5 mL), was added pyridine (0.052 mL, 0.64 mmol, 2.0 eq). The aniline was titrated with benzoyl chloride (0.037 mL, 0.32 mmol, 1.0 eq), in three portions, at 0° C. The reaction mixture was allowed to warm to ambient temperature, diluted with ethyl acetate (35 mL) then washed with saturated aqueous sodium bicarbonate solution (20 mL). The residue was purified by flash chromatography (20:1 CHCl₃:MeOH, 0.5% TEA) to give the intermediate amide (55 mg, 0.132 mmol, 41%). The amide (55 mg, 0.132 mmol) was dissolved in o-xylene (1 mL) then heated at 150° C., following the reaction by tlc (9:1 CHCl₃:MeOH, 1% TEA). Once the amide had been consumed, the reaction was allowed to cool to ambient temperature. The solvent was removed under reduced pressure. After flash chromatography (eluting with 20:1 CHCl₃:MeOH, 0.5% TEA) to obtain the benzimidazole as a glass (22.2 mg, 43%), the oxalate salt was formed by dissolution in ethyl acetate (1 mL) followed by the addition of a solution of oxalic acid in ethyl acetate (0.558 mL of 0.1M, 1.0 eq). The solvent was removed under reduced pressure to give the title salt as a tan glass (27 mg, 100%).

¹HNMR (300 MHz, CDCl₃) δ7.89 (d, J=9.0 Hz, 1H), 7.73–7.69 (m, 2H), 7.43–7.48 (m, 2H), 7.35–7.25 (m, 5H), 6.70 (d, J=6.0 Hz, 1H), 6.56 (s, 1H), 5.44 (s, 2H), 3.71 (s, 2H), 3.67 (s, 3H), 1.83 (bm, 4H), 1.26 (bm, 4H); FDMS m/e 397.2 (M+); FABHRMS cal'c for C₂₆H₂₈N₅O: 398.2239, found: 398.2232.

What is claimed is:
1. A method of inhibiting thrombin comprising using an effective amount of a thrombin inhibiting compound of formula I, or a pharmaceutically acceptable salt thereof,

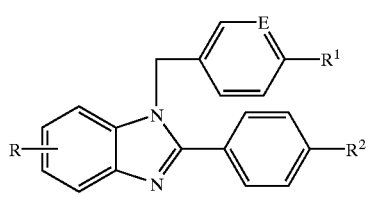

I wherein
  E is CH or CR^e in which R^e is methyl, methoxy or halo;
  R denotes 0, 1 or 2 substituents on the benz-ring independently selected from halo, methyl, ethyl, hydroxy, methoxy, carbamoyl, aminomethyl and hydroxymethyl;

$R^1$ is $R^{1a}$, $R^{1b}$, or $R^{1c}$ in which
  $R^{1a}$ is —$CH_2$—$R^r$, in which $R^r$ is 5-tetrazolyl, 2-carboxypyrrolidin-1-yl or 2-[[(1–4C)alkoxy]carbonyl]-pyrrolidin-1-yl; 2-carboxy-5-oxopyrrolidin-1-yl or 2-[[(1–4C)alkoxy]carbonyl]-5-oxopyrrolidin-1-yl;
  $R^{1b}$ is —$X^1$—$(CH_2)_s$—$NR^sR^t$ in which $X^1$ is a direct bond, methylene or O; s is 1 or 2; provided that when s is 1, then $X^1$ is a direct bond, and further provided that the chain —$(CH_2)_s$— may bear one or two methyl or ethyl substituents or may be part of a trans-1,2-cyclohexanediyl; and $R^s$ and $R^t$ are independently hydrogen or (1–3C)alkyl or the group $NR^sR^t$ is pyrrolidino, piperidino, morpholino, 1-imidazolyl, 1-pyrazolyl, 1,2,4-triazol-1-yl, or benzylamino; and
  $R^{1c}$ is —$X^1$—$(CH_2)_s$—$NR^sR^t$ in which $X^1$ is a direct bond, methylene or O; s is 1 or 2; provided that when s is 1, then $X^1$ is a direct bond, and further provided that the chain —$(CH_2)_s$— may bear one or two methyl or ethyl substituents or may be part of a trans-1,2-cyclohexanediyl; and the group $NR^sR^t$ is 2-oxopyrrolidin-1-yl, 2,5-dioxopyrrolidin-1-yl, 2-oxooxazolidin-3-yl, 2-oxoimidazolidin-1-yl, 3-methyl-2-oxoimidazolidin-1-yl, 2-oxopyrrolidin-3-yl, 1-methyl-2-oxopyrrolidin-3-yl, 1-tetrazolyl, methylsulfonylamino or phenylsulfonylamino; and
$R^2$ is $R^{2a}$, $R^{2b}$, or $R^{2c}$ in which
  $R^{2a}$ is —$X^2$—$(CH_2)_n$—$R^f$ in which $X^2$ is a direct bond, methylene or O; n is 1, 2 or 3; and $R^f$ is 5-tetrazolyl, carboxy, [(1–4C)alkoxy]carbonyl or hydroxymethyl; or (provided that when n is 1, $X^2$ is a direct bond) $R^f$ is 2-carboxypyrrolidin-1-yl, 2-[[(1–4C)alkoxy]carbonyl]-pyrrolidin-1-yl, (carboxymethyl)amino, [[(1–4C)alkoxy]-carbonylmethyl]amino, (4-carboxymethylimidazol-1-yl)amino, [4-[[(1–4C)alkoxy]carbonylmethyl]imidazol-1-yl]amino, (4-carboxybenzyl)amino, [4-[[(1–4C)alkoxy]carbonyl]benzyl]-amino, (3-amino-1,4-dioxo-4-hydroxybutyl)amino or [3-amino-1,4-dioxo-[(1–4C)alkoxy]butyl]amino;
  $R^{2b}$ is —$X^2$—$(CH_2)_m$—$NR^aR^b$ in which $X^2$ is a direct bond, methylene, O or S; m is 1, 2, 3, 4 or 5; provided that when m is 1, then $X^2$ is a direct bond; and $R^a$ and $R^b$ are independently hydrogen, or (1–3C)alkyl, or one of $R^a$ and $R^b$ is hydrogen or methyl and the other is t-butyl, benzyl, or pyridylmethyl; or the group $NR^aR^b$ is pyrrolidino, piperidino, morpholino, 1-imidazolyl, 1-pyrazolyl, or 1,2,4-triazol-4-yl; or
  $R^{2b}$ is —[$X^2$—$(CH_2)_n$]$_p$—$N(R^a)$—CO—A in which $X^2$ is a direct bond, methylene or O; n is 1, 2, 3 or 4; p is 0 or 1, $R^a$ is hydrogen or methyl; and —CO—A is an α-amino acyl group derived from an α-amino acid selected from glycine, alanine, valine, leucine, isoleucine, phenylalanine, tyrosine, serine, threonine, methionine, cysteine, proline, azetidine-2-carboxylic acid, pipecolic acid, aspartic acid, asparginine, glutamic acid, glutamine, lysine, arginine, and histidine in which an amino group may bear a t-butoxycarbonyl protecting group; a carboxy group may be protected as its (1–4C)alkyl ester; a hydroxy group may bear a benzyl protecting group; and a thiol group may bear a t-butyl protecting group; or
  the α-amino acyl group —CO—A is represented as —CO—CH($R^b$)—$NR^fR^g$, in which $R^b$ is the side chain of an α-amino acyl group derived from an α-amino acid selected from glycine, alanine, valine, leucine, isoleucine, phenylalanine, tyrosine, serine, threonine, methionine, cysteine, aspartic acid, asparginine, glutamic acid, glutamine, lysine, arginine, and histidine in which an amino group may bear a t-butoxycarbonyl protecting group; a carboxy group may be protected as its (1–4C)alkyl ester; a hydroxy group may bear a benzyl protecting group; and a thiol group may bear a t-butyl protecting group; and each of $R^f$ and $R^g$ is hydrogen or methyl, or —$NR^fR^g$ is a pyrrolidino, piperidino, morpholino or 1,1-dioxothiomorpholin-4-yl group; and
  $R^{2c}$ is hydrogen, or
  $R^{2c}$ is —$NR^a$—CO—$(CH_2)_m$—$R^b$ or —O—$CH_2$—$R^b$ in which m is 0 or 1, $R^a$ is hydrogen or methyl, and $R^b$ is a ring of formula XII or formula XIII

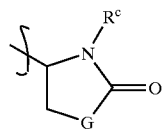

XII

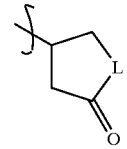

XIII in which G is O, S, NH or $CH_2$ and $R^c$ is hydrogen or methyl, and L is $NR^f$ or $CH_2$ and $R^f$ is hydrogen or methyl; or
  $R^{2c}$ is —$NHCOR^g$ in which $R^g$ is a five-membered heteroaromatic ring having 2 heteroatoms selected from O, S and N and in which the carbonyl group is bonded to a ring carbon situated between a ring heteroatom and another ring carbon; or
  $R^{2c}$ is —$(CH_2)_n$—$R^h$, —O—$(CH_2)_n$—$R^h$ or —NH—$(CH_2)_n$—$R^h$ in which n is 0, 1 or 2 and $R^h$ is cyclopentyl, cyano, or —$CONR^iR^j$ in which $R^i$ and $R^j$ are independently hydrogen or methyl or the group $NR^iR^j$ is pyrrolidino, piperidino, or morpholino; or
  $R^{2c}$ is —$X^2$—$(CH_2)_p$—$R^k$, or —O—$CH_2$—CH$(CH_3)$—$R^k$ in which $X^2$ is a direct bond, methylene or O and p is 1, 2 or 3, provided that when p is 1, then $X^2$ is a direct bond, and $R^k$ is 2-oxopyrrolidin-1-yl or $NHCOR^m$ in which $R^m$ is (1–3C)alkyl, phenyl or pyridyl; or
  $R^{2c}$ is —NH—CO—$NR^iR^j$ in which $R^i$ and $R^j$ are independently hydrogen or methyl or the group $NR^iR^j$ is pyrrolidino, piperidino, or morpholino; or
  $R^{2c}$ is —O—CO—$NR^pR^q$ in which $R^p$ and $R^q$ are independently hydrogen, methyl or ethyl or the group $NR^pR^q$ is pyrrolidino, piperidino, or morpholino; or
  $R^{2c}$ is —NH—$SO_2$—$R^r$ in which $R^r$ is (1—3C)alkyl or phenyl; and
provided that either $R^1$ is $R^{1b}$ or $R^2$ is $R^2b$.

2. The method of claim 1 in which the compound of formula I is a compound of formula Ia

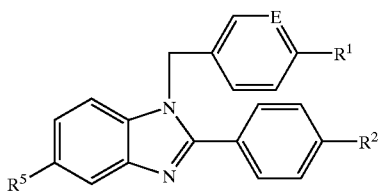

wherein

E is CH or CR$^e$ in which R$^e$ is methyl, methoxy or halo;

R$^1$ is —X$^1$—(CH$_2$)$_s$—NR$^s$R$^t$ in which X$^1$ is a direct bond, methylene or O; s is 1 or 2; provided that when s is 1, then X$^1$ is a direct bond; and R$^s$ and R$^t$ are independently hydrogen or (1–3C)alkyl or the group NR$^s$R$^t$ is pyrrolidino, piperidino, morpholino, 1-imidazolyl, 1-pyrazolyl, 1,2,4-triazol-1-yl, or benzylamino;

R$^2$ is hydrogen or —X$^2$—(CH$_2$)$_m$—NR$^a$R$^b$ in which X$^2$ is a direct bond, methylene, O or S; m is 1, 2, 3, 4 or 5; provided that when m is 1, then X$^2$ is a direct bond; and R$^a$ and R$^b$ are independently hydrogen or (1–3C)alkyl or the group NR$^a$R$^b$ is pyrrolidino, piperidino, morpholino, 1-imidazolyl; 1-pyrazolyl, 1,2,4-triazol-4-yl or 2-oxopyrrolidin-1-yl; and R$^5$ is hydrogen, hydroxy or methoxy.

3. The method of claim 2 in which —X$^1$—(CH$_2$)$_s$—NR$^s$R$^t$ is —CH$_2$—NR$^s$R$^t$ in which NR$^s$R$^t$ is pyrrolidino, 1-imidazolyl, 1-pyrazolyl, 1,2,4-triazol-1-yl, or benzylamino or is —O—(CH$_2$)$_2$—NR$^s$R$^t$ in which NR$^s$R$^t$ is pyrrolidino.

4. The method of claim 3 in which —X$^1$—(CH$_2$)$_s$—NR$^s$R$^t$ is —CH$_2$—NR$^s$R$^t$.

5. The method of claim 2 in which R$^2$ is —O—(CH$_2$)$_2$—NR$^a$R$^b$ in which NR$^a$R$^b$ is pyrrolidino, 1-pyrazolyl or 2-oxopyrrolidin-1-yl.

6. The method of claim 2 in which R$^5$ is hydroxy.

7. The method of any one of claims 1 and 2–6 in which halo is fluoro, chloro, bromo or iodo; a (1–3C)alkyl group is methyl, ethyl, propyl or isopropyl; a (1–4C)alkyl group is methyl, ethyl, propyl, isopropyl or butyl; and a (1–4C) alkoxy group is methoxy, ethoxy, isopropoxy or t-butoxy.

8. The method of claim 1 wherein the salt is selected from an acid addition salt of a compound of formula I or a salt of a compound of formula I made with a base.

9. A compound selected from the group consisting of:

(i) 5-hydroxy-1-[3-methoxy-4-[(1,2,4-triazol-1-yl)-methyl]benzyl]-2-[4-[2-(1-pyrrolidinyl)ethoxy]phenyl]-benzimidazole, (ii) 5-hydroxy-1-[4-[(1-imidazolyl)methyl]-3-methoxybenzyl]-2-[4-[2-(1-pyrrolidinyl)ethoxy]phenyl]benzimidazole, (iii) 5-hydroxy-1-[3-methoxy-4-[(1-pyrazolyl)methyl]-benzyl]-2-[4-[2-(1-pyrrolidinyl)ethoxy]phenyl]benzimidazole, (iv) 1-[4-(benzylamino)methyl-3-methoxybenzyl]-5-hydroxy-2-[4-[2-(1-pyrrolidinyl)ethoxy]phenyl]-benzimidazole, (v) 1-[4-[2-(1-pyrrolidinyl)ethoxy]benzyl]-2-[4-[2-(1-pyrrolidinyl)ethyoxy]phenyl]benzimidazole, (vi) 1-[3-methoxy-4-(1-pyrrolidinyl)methylbenzyl]-2-[4-[2-(1-pyrazolyl)ethoxy]phenyl]benzimidazole, and (vii) 1-[3-methoxy-4-[(1-pyrrolidinyl)methyl]benzyl]-2-[4-[2-(2-oxopyrrolidin-1-yl)ethoxy]phenyl]benzimidazole, or a pharmaceutically acceptable salt thereof.

10. A pharmaceutical composition comprising in association with a pharmaceutically acceptable carrier, diluent or excipient, a compound selected from the group consisting of:

(i) 5-hydroxy-1-[3-methoxy-4-[(1,2,4-triazol-1-yl)-methyl]benzyl]-2-[4-[2-(1-pyrrolidinyl)ethoxy]phenyl]-benzimidazole, (ii) 5-hydroxy-1-[4-[(1-imidazolyl)methyl]-3-methoxy-benzyl]-2-[4-[2-(1-pyrrolidinyl)ethoxy]phenyl]benzimidazole, (iii) 5-hydroxy-1-[3-methoxy-4-[(1-pyrazolyl)methyl]-benzyl]-2-[4-[2-(1-pyrrolidinyl)ethoxy]phenyl]benzimidazole, (iv) 1-[4-(benzylamino)methyl-3-methoxybenzyl]-5-hydroxy-2-[4-[2-(1-pyrrolidinyl)ethoxy]phenyl]-benzimidazole, (v) 1-[4-[2-(1-pyrrolidinyl)ethoxy]benzyl]-2-[4-[2-(1-pyrrolidinyl)ethyoxy]phenyl]benzimidazole, (vi) 1-[3-methoxy-4-(1-pyrrolidinyl)methylbenzyl]-2-[4-[2-(1-pyrazolyl)ethoxy]phenyl]benzimidazole, and (vii) 1-[3-methoxy-4-[(1-pyrrolidinyl)methyl]benzyl]-2-[4-[2-(2-oxopyrrolidin-1-yl)ethoxy]phenyl]benzimidazole, or a pharmaceutically acceptable salt thereof.

* * * * *